(12) United States Patent
Mao et al.

(10) Patent No.: US 10,472,621 B2
(45) Date of Patent: Nov. 12, 2019

(54) NUCLEIC ACID EXTRACTION APPARATUS

(71) Applicant: LEADWAY (HK) LIMITED, Hong Kong (CN)

(72) Inventors: Haiming Mao, Zhejiang (CN); Zijian Luo, Zhejiang (CN); Tao Wang, Zhejiang (CN); Chun Yu, Zhejiang (CN); Tao Lin, Zhejiang (CN)

(73) Assignee: Leadway (HK) Limited, Hong Kong (HK)

( * ) Notice: Subject to any disclaimer, the term of this patent is extended or adjusted under 35 U.S.C. 154(b) by 376 days.

(21) Appl. No.: 15/033,569

(22) PCT Filed: Oct. 31, 2014

(86) PCT No.: PCT/CN2014/090127
§ 371 (c)(1),
(2) Date: Apr. 29, 2016

(87) PCT Pub. No.: WO2015/062548
PCT Pub. Date: May 7, 2015

(65) Prior Publication Data
US 2016/0289665 A1    Oct. 6, 2016

(30) Foreign Application Priority Data
Nov. 1, 2013   (CN) .......................... 2013 1 0531474

(51) Int. Cl.
*C12N 15/10*    (2006.01)
*C12M 1/00*    (2006.01)
(Continued)

(52) U.S. Cl.
CPC ......... *C12N 15/1013* (2013.01); *C12M 47/06* (2013.01); *G01N 35/0099* (2013.01);
(Continued)

(58) Field of Classification Search
CPC ............... C12M 47/06; C12N 15/1013; G01N 35/00584; G01N 2035/00306;
(Continued)

(56) References Cited

U.S. PATENT DOCUMENTS

| 7,329,488 | B2 | 2/2008 | Roh et al. |
| 7,541,001 | B2 * | 6/2009 | Kraemer ............. G01N 35/109 422/561 |

(Continued)

FOREIGN PATENT DOCUMENTS

| CN | 2724291 Y | 9/2005 |
| CN | 2890059 Y | 4/2007 |

(Continued)

OTHER PUBLICATIONS

First OA issued in Chinese Patent Application No. 201410004580.1 dated Feb. 10, 2015—incl Engl lang transl.
(Continued)

*Primary Examiner* — Shogo Sasaki
(74) *Attorney, Agent, or Firm* — Acuity Law Group, PC; Michael A. Whittaker

(57) ABSTRACT

The present invention provides a nucleic acid extraction instrument including a base, an outer housing connected with the base, and an instrumental main body positioned inside the outer housing and mounted to the base; and the instrumental main body includes an electrical power pack, a main control device, a first motor set, a second motor set, and a third motor set.

5 Claims, 34 Drawing Sheets

(51) Int. Cl.
   *G01N 35/00* (2006.01)
   *G01N 35/10* (2006.01)
(52) U.S. Cl.
   CPC ... *G01N 35/00584* (2013.01); *G01N 35/0098* (2013.01); *G01N 2035/00306* (2013.01); *G01N 2035/00534* (2013.01); *G01N 2035/1053* (2013.01)
(58) Field of Classification Search
   CPC ........... G01N 35/0098; G01N 35/0099; G01N 2035/00534; G01N 2035/1053
   See application file for complete search history.

(56) References Cited

U.S. PATENT DOCUMENTS

| | | | |
|---|---|---|---|
| 7,879,292 | B2* | 2/2011 | Nagai ................ B01F 11/0008 366/111 |
| 2003/0215361 | A1 | 11/2003 | Jang et al. |
| 2004/0029291 | A1 | 2/2004 | Franzreb et al. |
| 2004/0157224 | A1 | 8/2004 | Roh et al. |
| 2007/0148785 | A1 | 6/2007 | Lutze |
| 2007/0221543 | A1 | 9/2007 | Karmeniemi et al. |
| 2008/0241914 | A1 | 10/2008 | Roh et al. |
| 2009/0176308 | A1 | 7/2009 | Griebel et al. |
| 2009/0220979 | A1 | 9/2009 | Davis et al. |

FOREIGN PATENT DOCUMENTS

| | | |
|---|---|---|
| CN | 201303287 Y | 9/2009 |
| CN | 201686641 U | 12/2010 |
| CN | 101952412 A | 1/2011 |
| CN | 102492603 A | 6/2012 |
| CN | 102660458 A | 9/2012 |
| CN | 203156509 U | 8/2013 |
| CN | 103305412 A | 9/2013 |
| CN | 203174009 U | 9/2013 |
| CN | 203174103 U | 9/2013 |
| CN | 103881892 A | 6/2014 |
| CN | 203768349 U | 8/2014 |
| EP | 1767623 A1 | 3/2007 |
| JP | 2005143324 A | 6/2005 |
| KR | 100720044 B1 | 5/2007 |
| WO | 9940444 A1 | 8/1999 |

OTHER PUBLICATIONS

Second OA issued in Chinese Patent Application No. 201410004580.1 dated Aug. 10, 2015—incl Engl lang transl.
Third OA issued in Chinese Patent Application No. 201410004580.1 dated Feb. 4, 2016—incl Engl lang transl.
Response to the First OA issued in Chinese Patent Application No. 201410004580.1 dated Jun. 18, 2015—incl Engl lang transl.
Response to the Second OA issued in Chinese Patent Application No. 201410004580.1 dated Oct. 18, 2015—incl Engl lang transl.
Response to the Third OA issued in Chinese Patent Application No. 201410004580.1 dated Apr. 18, 2016—incl Engl lang transl.
First OA issued in Chinese Patent Application No. 201420005539.1 dated Sep. 17, 2014—incl Engl lang transl.
Response to the First OA issued in Chinese Patent Application No. 201420005539.1 dated Dec. 1, 2014—incl Engl lang transl.
First OA issued in Chinese Patent Application No. 201410004527.1 dated Mar. 13, 2015—incl Engl lang transl.
Response to the First OA issued in Chinese Patent Application No. 201410004527.1 dated Jul. 23, 2015—incl Engl lang transl.
Second OA issued in Chinese Patent Application No. 201410004527.1 dated Oct. 19, 2015—incl Engl lang transl.
Response to the Second OA issued in Chinese Patent Application No. for 201410004527.1 dated Dec. 28, 2015—incl Engl lang transl.
First OA issued in Chinese Patent Application No. 201410004539.4 dated Feb. 11, 2015—incl Engl lang transl.
Second OA issued in Chinese Patent Application No. 201410004539.4 dated Aug. 27, 2015—incl Engl lang transl.
Response to the First OA issued in Chinese Patent Application No. 201410004539.4 dated Jun. 23, 2015—incl Engl lang transl.
Response to the Second OA issued in Chinese Patent Application No. for 201410004539.4 dated Oct. 8, 2015—incl Engl lang trans.
First OA issued in Chinese Patent Application No. 201410004235.8 dated Feb. 5, 2015—incl Engl lang transl.
Second OA issued in Chinese Patent Application No. 201410004235.8 dated Aug. 10, 2015—incl Engl lang transl.
Third OA issued in Chinese Patent Application No. 201410004235.8 dated Feb. 4, 2016 —incl Engl lang transl.
Single-chip controlled stepping motor synchronous follower system design. Sep. 2008:144-147 (3rd OA for Chinese Patent Application No. 201410004235.8)—incl Engl lang transl.
Response to the First OA issued in Chinese Patent Application No. 201410004235.8 dated Jun. 16, 2015—incl Engl lang transl.
Response to the Second OA issued in Chinese Patent Application No. 201410004235.8 dated Oct. 23, 2015—incl Engl lang transl.
Response to the Third OA issued in Chinese Patent Application No. 201410004235.8 dated Apr. 15, 2016—incl Engl lang transl.
First OA issued in Chinese Patent Application No. 201410004609.6 dated Feb. 17, 2015—incl Engl lang transl.
Second OA issued in Chinese Patent Application No. 201410004609.6 dated Oct. 19, 2015—incl Engl lang transl.
Response to the First OA issued in Chinese Patent Application No. 201410004609.6 dated Jun. 30, 2015—incl Engl lang transl.
Response to the Second OA issued in Chinese Patent Application No. 201410004609.6 dated Jan. 4, 2016—incl Engl lang transl.
First OA issued in Chinese Patent Application No. 201410003982.X dated Feb. 16, 2015—incl Engl lang transl.
Second OA issued in Chinese Patent Application No. 201410003982.X dated Sep. 9, 2015—incl Engl lang transl.
Response to the First OA issued in Chinese Patent Application No. 201410003982.X dated Jun. 29, 2015—incl Engl lang transl.
Response to the Second OA issued in Chinese Patent Application No. 201410003982.X dated Nov. 23, 2015—incl Engl lang transl.
International Search Report and Written Opinion issued in PCT/CN2014/090127 dated Feb. 10, 2015—incl Engl lang transl.
International Search Report and Written Opinion issued in PCT/CN2014/090128 dated Jan. 14, 2015—incl Engl lang transl.
International Search Report and Written Opinion issued in PCT/CN2014/090129 dated Feb. 2, 2015—incl Engl lang transl.
International Search Report and Written Opinion issued in PCT/CN2014/090130 dated Feb. 10, 2015—incl Engl lang transl.
International Search Report and Written Opinion issued in PCT/CN2014/090131 dated Feb. 16, 2015—incl Engl lang transl.
Supplementary European Search Report and Written Opinion issued in EP14858908 dated Jun. 6, 2017.
Extended European Search Report and Written Opinion issued in EP14858908 dated May 16, 2017.
Response to Extended European Search Report and Written Opinion issued in EP14858908 dated Dec. 8, 2017.

* cited by examiner

NUCLEIC ACID EXTRACTION APPARATUS

CROSS-REFERENCE TO RELATED APPLICATIONS

The present invention is filed under 35 U.S.C. § 371 as the U.S. national phase of International Application No. PCT/CN2014/090127, filed Oct. 31, 2014, which designated the U.S. and claims the benefit of priority to Chinese Patent Application No. 201310531474.4, filed Nov. 1, 2013, each of which is hereby incorporated in its entirety including all tables, figures, and claims.

BACKGROUND OF THE INVENTION

Field of the Invention

The present invention relates to a nucleic acid extraction instrument.

Description of the Related Art

In study fields of genetic engineering and protein engineering technologies, a nucleic acid molecule is a main subject of study, and isolation and linearization of nucleic acid are basic technologies of nucleic acid research. The nucleic acid is a basic unit representing genetic characteristics of a life entity, and nucleic acid detection is advanced biological detection performed in a molecular level and has remarkable advantages of high sensitivity, high specificity, no window period and so on, compared with a conventional morphological detection, cytological detection, immunological detection and the like. The nucleic acid detection includes technologies such as qualitative polymerase chain reaction (PCR), molecular hybridization, real-time fluorescence quantification PCR and so on, and first critical aspects of these nucleic acid detection technologies are to complete extraction of the nucleic acid of a biological sample. Therefore, effectively and accurately extracting a nucleic acid template becomes a premise of subsequent nucleic acid detection. At present, nucleic acid extraction in China mainly adopts a conventional manual manufacture and preparation method, which is low in efficiency, high in cost, and poor in repeatability and stability.

BRIEF SUMMARY OF THE INVENTION

An objective of the present invention is to provide a nucleic acid extraction instrument and particularly to a fully automatic nucleic acid extraction instrument.

The nucleic acid extraction instrument of the present invention includes a base, an outer housing connected with the base, an instrumental main body positioned inside the outer housing and mounted to the base. The instrumental main body includes an electrical power pack, a main control device, a first motor set, a second motor set, and a third motor set.

Further, a lengthwise direction of the first motor set may be approximately parallel to an upper surface of the base, and lengthwise directions of the second motor set and the third motor set may be approximately perpendicular to the upper surface of the base.

Further, the first motor set may be fixed to the base, the first motor set may include a motor fixed on the base and incapable of generating a relative displacement relative to the base, a ball screw coaxially connected with a shaft of the motor via a connector, a sliding block connected to the ball screw, and a guide rail playing a guiding role for the sliding block.

Further, the second motor set and the third motor set may be fixed to a sliding block of the first motor set and reciprocate along an axial direction of the motor under a drive of the first motor set.

Further, the second motor set and the third motor set may be fixed to the sliding block of the first motor set via a motor bracket. The motor bracket may include a first panel and a second panel, which are approximately perpendicular to each other. The first panel may be configured to fix the second motor set and the third motor set, and the second panel may be fixed to the sliding block on the first motor set.

Further, when the sliding block reciprocates along an axial line of the ball screw, the sliding block may drive the motor bracket, the second motor set, and the third motor set to reciprocate between a first position and a second position in a plane parallel to a bottom plate and a lengthwise direction of an operating platform.

Further, the first motor set may output a movement in a direction approximately parallel to a certain plane of the base, and the second motor set and the third motor set may output a movement in a direction approximately perpendicular to the plane of the base.

Further, the nucleic acid extraction instrument may further include a bottom plate, an inner housing, a portal frame, and an operating platform, which are fixed to the base.

The present invention has the following beneficial effects:

1. Compared with the prior art, an extraction efficiency of hepatitis B virus (HBV) is increased by 2-4 times, a concentration of the extracted HBV is increased by 2-4 times, and therefore, the extracted HBV can be used for hypersensitivity detection. The reason for this is that the present invention adopts a moveable heating device, a plurality of springs is disposed below a heating plate, and after a deep well plate is placed on the heating plate, a bottom of the deep well plate extrudes the heating plate downward. Thus, the deep well plate and the heating plate can be attached to each other better. Accordingly, each well is uniformly heated, a temperature difference is small, and samples in respective wells are relatively uniform in lysing speeds and degrees in comparison with the prior art. In addition, a magnetic bar sleeve is made of a hydrophobic material, and thus magnetism attracting efficiency, demagnetizing efficiency, and mechanical stirring efficiency thereof are high and uniform. Moreover, the present invention adopts a step motor with a higher frequency than that of the prior art and a ball screw with a higher precision than that of the prior art as a transmission system. Thus, movement precisions of the magnetic bar sleeve and a magnetic bar are higher than those of the prior art, a mechanical stirring efficiency of the magnetic bar sleeve is higher, and the magnetic bar is controlled accurately without touching a wall and touching a magnetic ball.

2. A recovery rate of the magnetic ball is very high and reaches above 98%.

3. The value of coefficient of variation (CV) (mean squared error) calculated from the concentration tests of extraction among wells is small and is smaller than that of the prior art at least by ½. A process consistency is good, a 96-well plate has a good positioning precision and a good temperature uniformity, and elasticity exists below a heating plate.

4. The nucleic acid extraction instrument is super silent. After the ball screw is adopted, the integral noise generated by the instrument is lower than 60 dB and even lower than 53 dB, while the noise generated by the instrument in the prior art is greater than 80 dB.

5. The nucleic acid extraction instrument is free of maintenance and refueling; the linear guide rail is made of a special material and is free of maintenance after running for 20 thousands kilometers; and the nucleic acid extraction instrument is long in service life, resistant to folding and high in reliability.

6. A wide voltage range design (110V-220V) is adopted so that the whole system is controlled by using a safe voltage and driven by power, and the safety is good.

7. A plurality of mutually parallel or crisscross tendons or ribs is designed on the outer housing to improve the strength of the outer housing. On the other hand, a guide rail is designed on the portal frame, a sliding block is designed at the motor bracket corresponding to the guide rail, and the sliding block is limited to slide in the guide rail. Such a design can not only improve the stability of the motor bracket in movement but also improve a protection function for the motor bracket by the nucleic acid extraction instrument of the present invention in transporting and conveying processes. Therefore, the nucleic acid extraction instrument in the present invention is very firm.

8. The instrumental main body of the nucleic acid extraction instrument in the present invention is basically enclosed by the base and the outer housing, while a bottom of the base is provided with an air outlet for a cross flow fan. In addition, the nucleic acid extraction instrument in the present invention is further provided with the inner housing and an operating panel. The inner housing and the operating panel basically limit the deep well plate in relatively closed space. The above structure design is very beneficial to preventing an external environment from influencing cleanness inside the instrument.

9. A power supply regulator included in the nucleic acid extraction instrument is used for converting an instantaneous overload voltage or overload current possibly generated during a running process of the nucleic acid extraction instrument into heat energy for being consumed so as to avoid burning the power supply regulator due to excessive temperature.

10. An encoder is disposed at the motor set in the present invention. The encoder can send a correction instruction according to a running condition of a step motor and timely corrects a stroke output by the step motor according to each pulse, thereby avoiding out of step of the motor in advance and improving the precision that the motor set drives a magnetic bar sleeve frame to vibrate.

11. An obstruction of placing the deep well plate on the operating platform may be reduced due to a clamping arm design of the present invention; a position of the deep well plate on the operating platform can be precisely fixed during a nucleic acid extraction process; and after the extraction process is finished, an operator can easily remove the deep well plate away from the operating platform.

12. Torsional springs on a door shaft of the nucleic acid extraction instrument enable joints between a door middle shaft and door shaft sleeves to keep having a certain damping coefficient, thereby increasing a hand feeling when a door is opened or closed and improving a pleasant feeling of the operator.

DETAILED DESCRIPTION OF THE INVENTION

The present invention will be described below in detail in connection with specific accompanying drawings. These specific embodiments are just a limited enumeration without departing from the spirit of the present invention, but not exclude other specific embodiments generated by combining the prior art with the present invention by the persons ordinarily skilled in the art.

Figure 1:
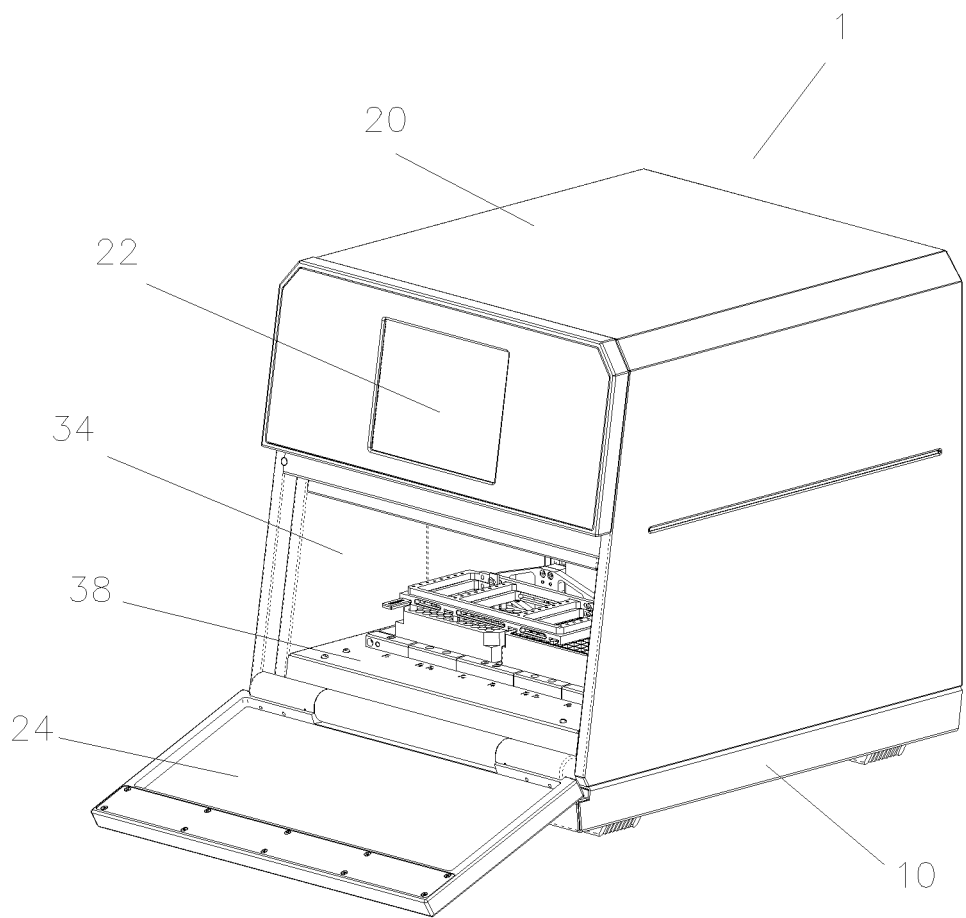
FIG. 1 is a schematic diagram showing a nucleic acid extraction instrument in the present invention.

As shown in FIG. 1, a nucleic acid extraction instrument 1 in the present invention includes a base 10 positioned at a bottom, an outer housing 20 positioned on the base, and an instrumental main body 30 positioned inside the outer housing 20 and fixed to the base 10. The base 10 is made of a material (such as cast iron, steel, a concrete-filled steel plate and so on) with relatively high specific weight and low cost, so that the base has a relatively high mass, thereby effectively preventing the nucleic acid extraction instrument from vibrating and moving in a running process. The outer housing 20 is preferably made of a stainless steel plate with a thickness of 0.1-2.0 mm processed and manufactured by techniques such as cold rolling, cold cutting and so on. In other solutions, the outer housing 20 may also be made of a plastic material manufactured by injection molding to reduce the cost. A plurality of mutually parallel or crisscross tendons or ribs may be designed on the outer housing 20 to improve the strength of the outer housing 20. Preferably, according to different selected materials, the outer housing 20 may be treated by techniques such as paint spraying, computer inkjet, computer carving, etching, electroplating and so on, so that the outer housing has a better appearance. The side of the outer housing 20 facing an operator, i.e. the front side of the nucleic acid extraction instrument 1, is designed with an instrumental panel 22 and a door 24 capable of being opened or closed for multiple times. A display screen and a plurality of operating keys may be designed on the instrumental panel 22, thus to facilitate operation by the operator. Preferably, a touch liquid crystal display screen is designed on the instrumental panel 22, thereby facilitating the operator to operate by directly touching the liquid crystal display screen.

Figure 2:
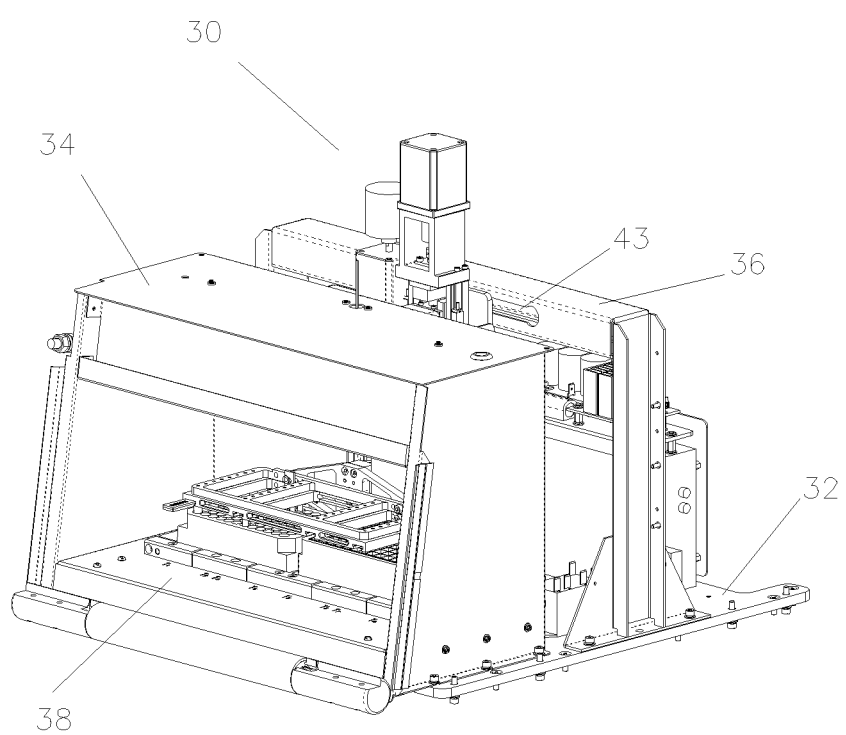
FIG. 2 is a schematic diagram of FIG. 1 after an outer housing and a base are removed.
Figure 3:
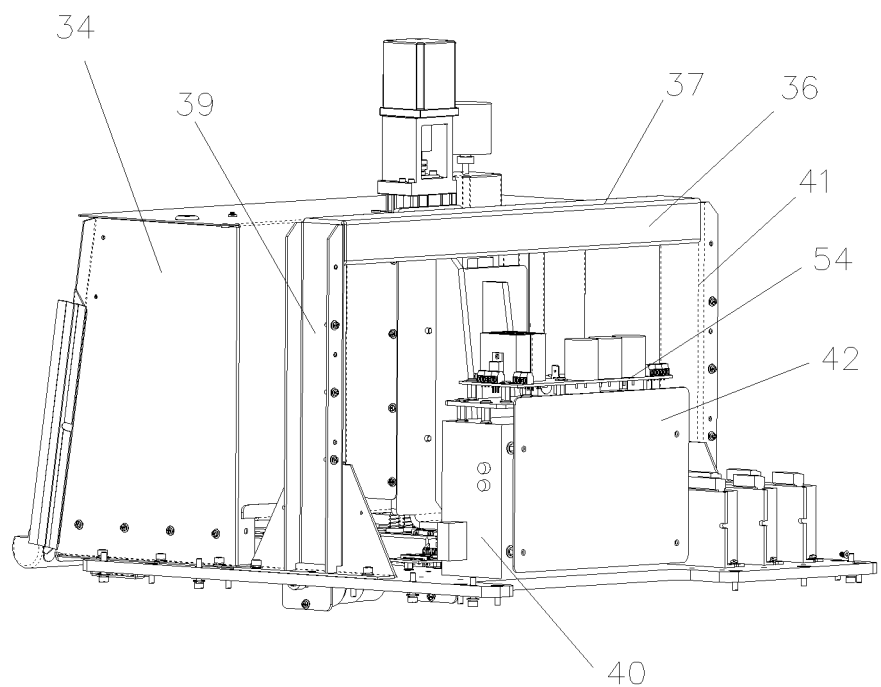
FIG. 3 is a schematic diagram of FIG. 2 in another viewing angle.
Figure 4:
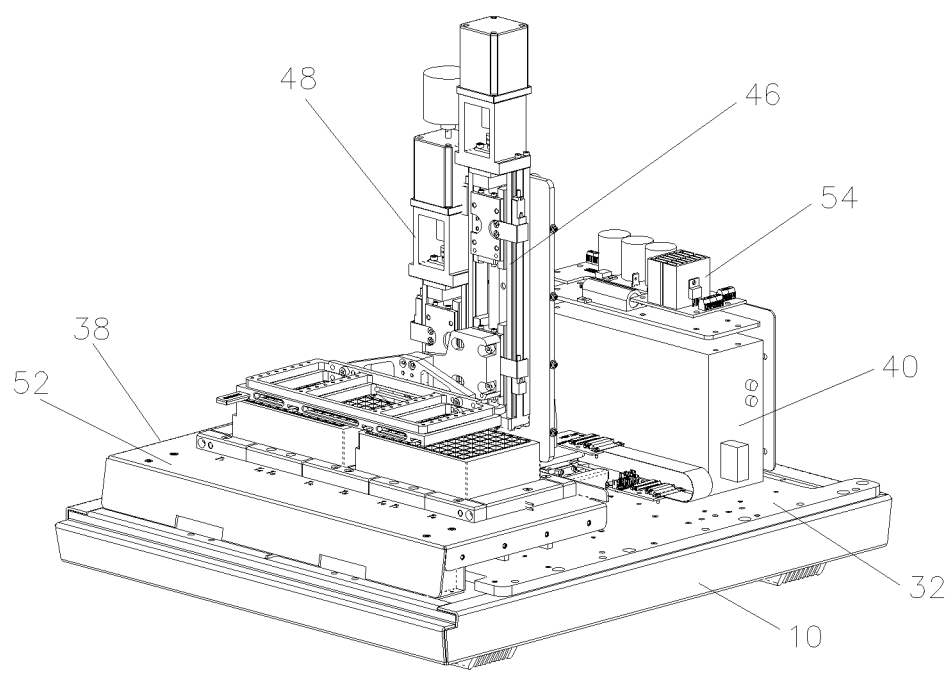
FIG. 4 is a schematic diagram showing the nucleic acid extraction instrument in the invention after an inner housing and the outer housing are removed.
Figure 5:
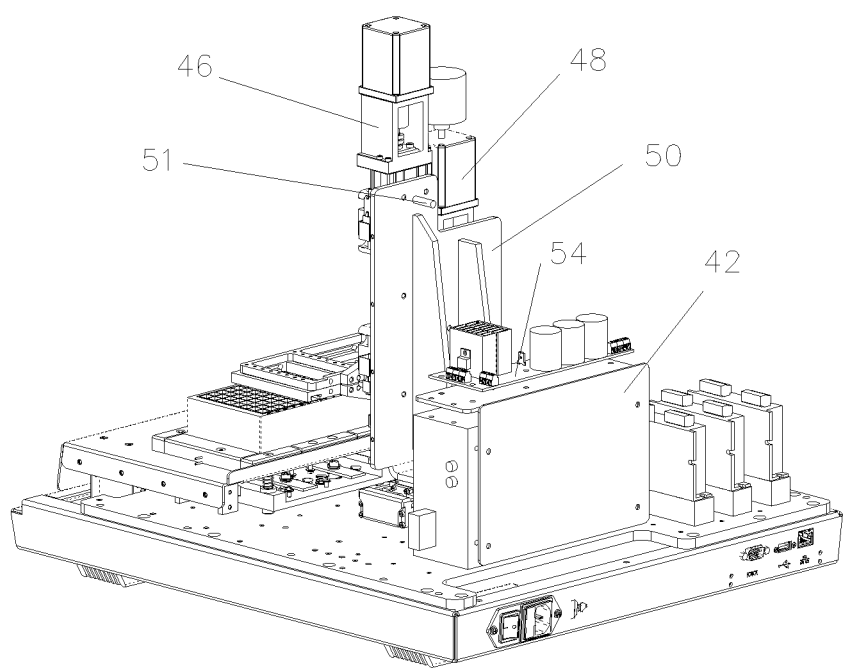
FIG. 5 is a schematic diagram of FIG. 4 in another viewing angle.
Figure 6:
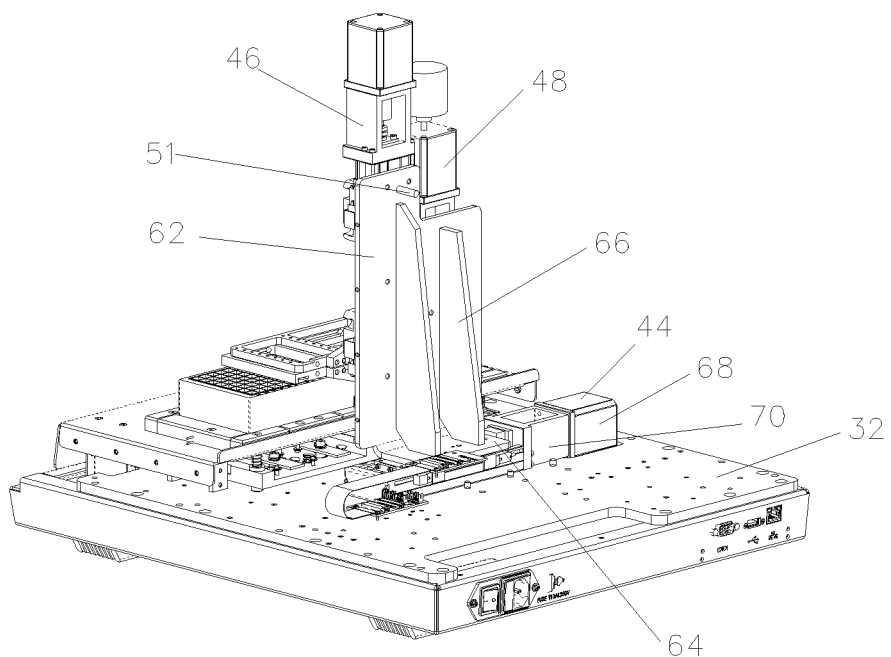
FIG. 6 is a schematic diagram of FIG. 5 after partial components are removed.
Figure 7:
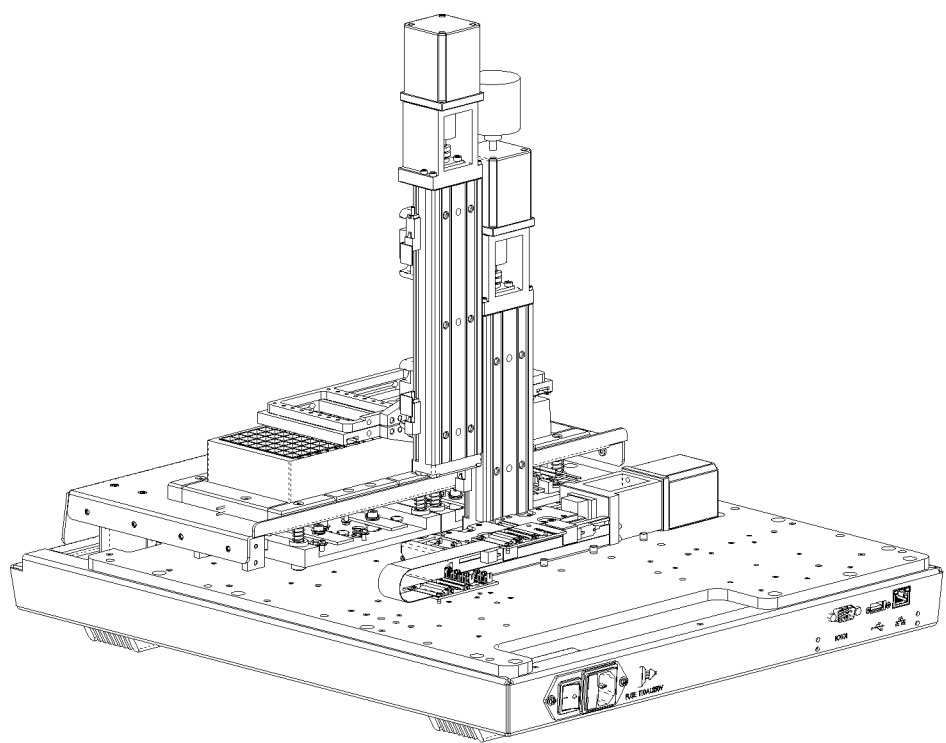
FIG. 7 is a schematic diagram of FIG. 6 after partial components are removed.

As shown in FIG. 2-FIG. 6, the instrumental main body 30 includes a bottom plate 32 fixed to the aforementioned base 10, an inner housing 34, a portal frame 36, an operating platform 38, a power pack 40, a main control device 42, a first motor set 44, a second motor set 46, and a third motor set 48. The bottom plate 32 provides at least one plane for supporting the aforementioned assembly. Preferably, the bottom plate 32 is a steel plate with a thickness of 1.0-10.0 mm, which should have a moderate rigidity and can keep at least one face be of a plane shape without easily being bent, twisted, partially upwarped and the like. To save the cost, under a condition of meeting the above requirements, the bottom plate 32 may be made of hard plastic by an injection molding process or may be made of hard wood or bamboo by a woodworking process. In one embodiment, when the bottom plate 32 has a sufficient thickness, rigidity, and mass, the bottom plate 32 may also serve as the base 10. Wherein, in one preferred embodiment, the inner housing 34, the portal frame 36, the operating platform 38, the power pack 40, and the first motor set 44 are fixed on the bottom plate 32, respectively. To save a space, the main control device 42 is disposed on a back face of the power pack 40 (as shown in FIG. 3). As shown in FIG. 6 and FIG. 7, the first motor set 44 is fixed on an upper surface of the bottom plate 32, and a lengthwise direction or an axial line of the first motor set 44 is parallel to the upper surface of the bottom plate. The second motor set 46 and the third motor set 48 are fixed to a motor bracket 50 at first and then installed on the first motor set 44 by the motor bracket 50. The second motor set 46 and the third motor set 48 are arranged adjacently and in parallel, axial lines of the second motor set 46 and the third motor set 48 are mutually parallel and are perpendicular to the upper surface of the bottom plate 32, respectively. A guide rail or a slide track 43 is designed on the portal frame 36, a sliding block 51 is designed at the motor bracket 50 corresponding to the guide rail 43, and the sliding block 51 is limited to slide in the guide rail 43. Such a design can not only improve the stability of the motor bracket 50 in movement but also improve a protection function for the motor bracket 50 by the nucleic acid extraction instrument of the present invention in transporting and conveying processes. In one implementing mode, the portal frame 36 includes at least one cross beam 37 and two vertical beams 39 and 41 for supporting the crossbeam 37. Wherein the guide rail 43 is designed on the cross beam 37, and the vertical beams 39 and 41 are fixed to the bottom plate 32 or the upper surface of the base 10, respectively.

As shown in FIG. 4, the operating platform 38 includes a flat and approximately cuboid-shaped operating panel 52 adjacent to a front face of the nucleic acid extraction instrument 1. The operating panel 52 should have suitable rigidity and strength and cannot be deformed easily. The operating panel 52 may be made of a stainless steel plate by a cold working process or may be made of hard plastic by an injection molding process. The operating panel 52 includes a platform approximately parallel to the upper surface of the bottom plate 32, and operations of extracting nucleic acid are basically completed on this platform. The platform includes two lengthwise sides approximately parallel to the front face of the nucleic acid extraction instrument 1. When the door 24 is in an open state, the operator can enter from the door 24 with two hands or one hand, the operations of extracting the nucleic acid are performed on the operating platform 38. The first motor set 44 is installed behind the operating platform 38 (that is a position further away from the front face of the nucleic acid extraction instrument than the operating platform 38, referring to FIG. 6 and FIG. 7). The lengthwise direction or an axial direction of the first motor set 44 is approximately parallel to a lengthwise side of the operating platform 38.

Figure 24:
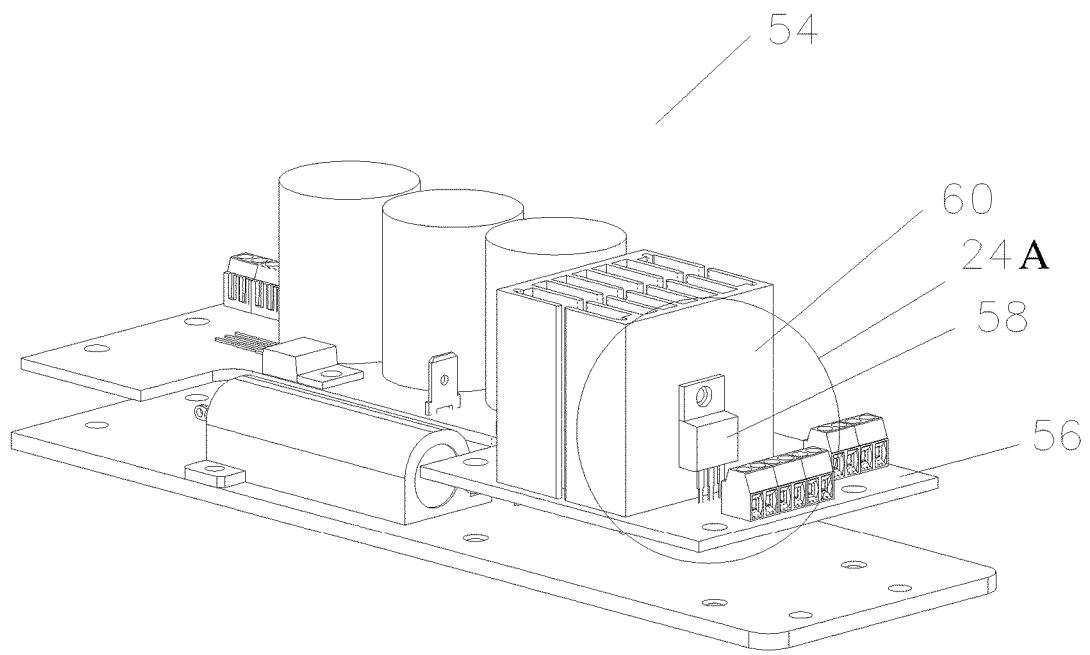
FIG. 24 is an enlarged schematic diagram of a power supply control component.
Figure 24A:
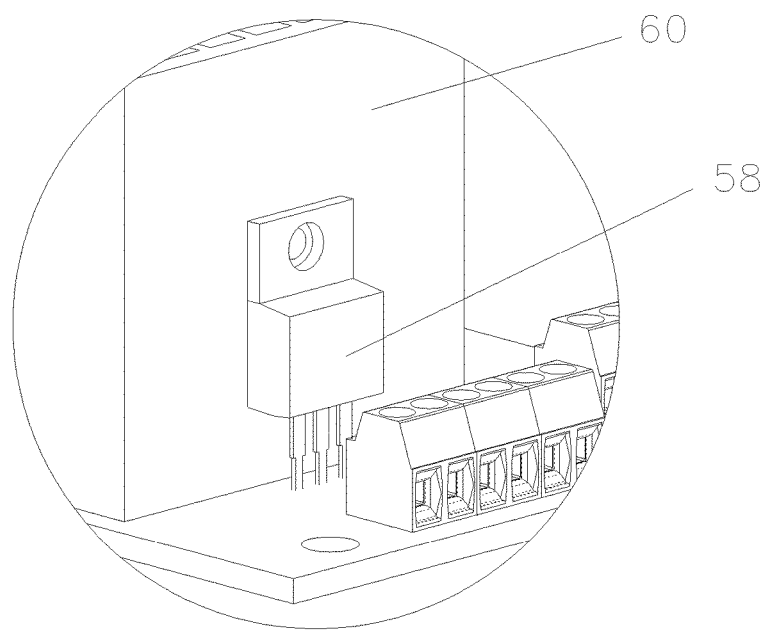
FIG. 24A is a partial enlarged view of FIG. 24.

The power pack 40 includes a component (unmarked) for converting a 220 V or 110 V general voltage into a voltage suitable for driving various electronic components inside the nucleic acid extraction instrument of the present invention and at least one set of power supply management assembly 54. To save the space, the power supply management assembly 54 is fixed above the power pack 40 (as shown in FIG. 4 and FIG. 5). Please refer to FIG. 24 and FIG. 24A, the power supply management assembly 54 includes at least one printed circuit board 56, a plurality of electronic components such as capacitors and resistors, at least one power supply regulator 58, and a heat radiator 60. The heat radiator 60 is closely against the power supply regulator 58. The power supply regulator 58 includes a heat emitting electronic component for converting an instantaneous overload voltage or overload current possibly generated during a running process of the nucleic acid extraction instrument into heat energy to be consumed. The heat radiator 60 is configured to timely transmit the heat energy generated by the power supply regulator 58, thereby cooling the power supply regulator 58 to avoid burning the power supply regulator 58 due to excessive temperature.

Figure 25:
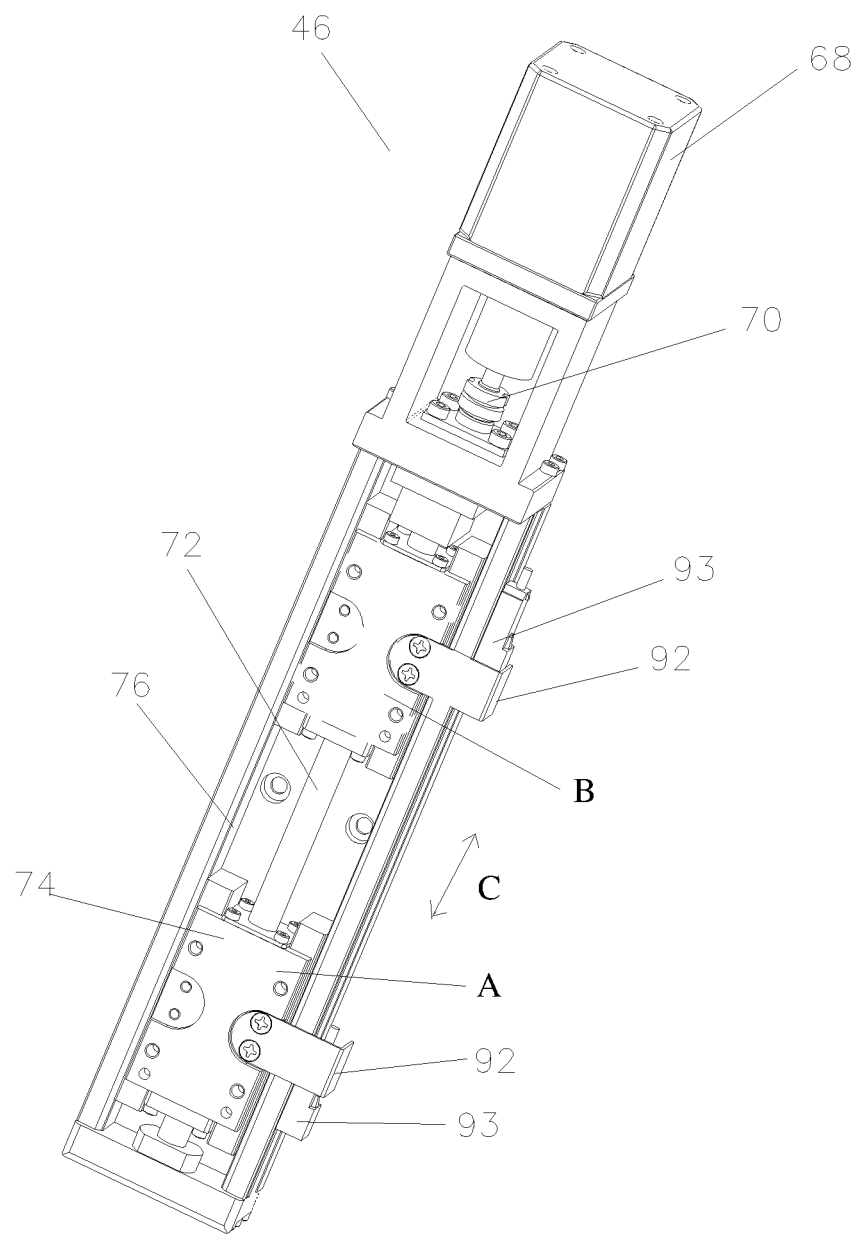
FIG. 25 is an enlarged schematic diagram of a first motor set.

As shown in FIG. 6, the motor bracket 50 includes a first panel 62 and a second panel 64 which are approximately perpendicular to each other, wherein the second motor 46 and the third motor set 48 are fixed on the first panel 62, and the second panel 64 is fixed to the first motor set 44. The motor bracket 50 may be made of a steel plate by a cold working process or may be made of hard plastic by an injection molding process. The motor bracket 50 is integrally approximately of an "L" shape. To improve the strength of the motor bracket 50, save materials, and reduce the weight, at least one tendon or rib 66 is disposed at the corner where the first panel 62 and the second panel 64 form an angle of approximately 90°. As shown in FIG. 6 and FIG. 25, the first motor set 44 includes a motor 68 which is fixed on the upper surface of the bottom plate 32 and cannot generate a relative displacement relative to the bottom plate 32, a ball screw 72 coaxially connected with a shaft of the motor 68 via a connector 70, a sliding block 74 connected to the ball screw 72, and a guide rail 76 playing a guiding role for the sliding block 74. When the first motor 44 works, the shaft of the motor 68 drives the ball screw 72 by the connector to rotate along an axial line thereof. The ball screw 72 rotates along the axial line to drive the sliding block 74 to reciprocate along the axial line of the ball screw 72. Because the second panel 64 of the motor bracket 50 is fixed to the sliding block 74 of the first motor set 44, when the sliding block 74 reciprocates along the axial line of the ball screw 72, the sliding block 74 drives the motor bracket 50, the second motor set 46, and the third motor set 48 reciprocate between a position "A" and a position "B" in a plane parallel to the bottom plate 32 and a lengthwise direction of the operating platform 38 (as shown in FIG. 25).

Figure 8:
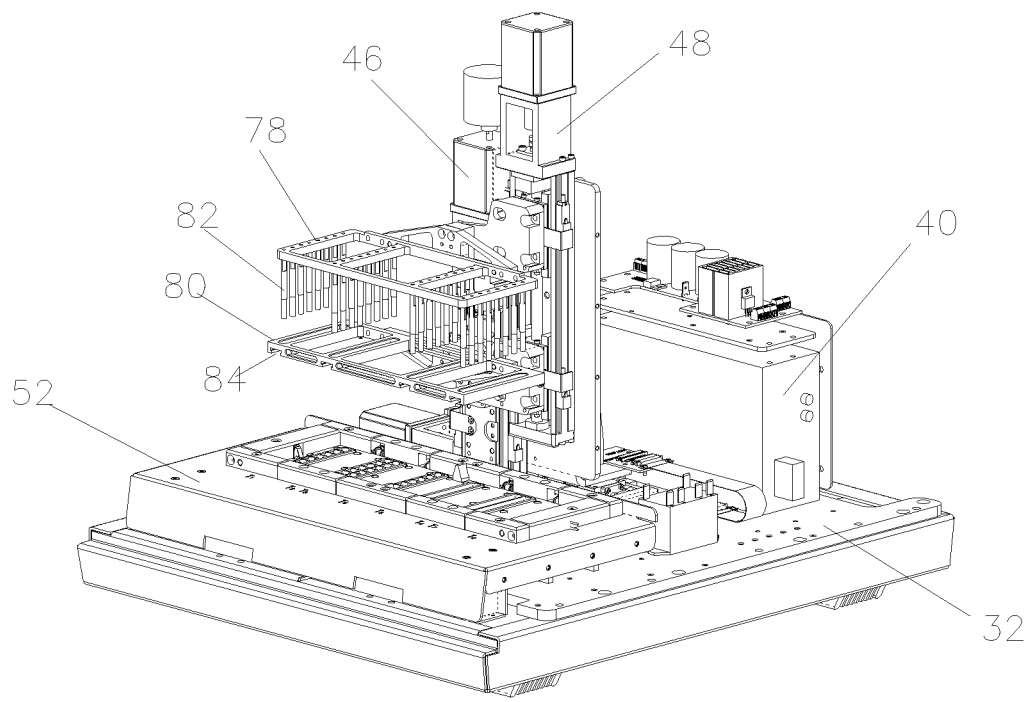
FIG. 8, similar to FIG. 4, is a schematic diagram showing the nucleic acid extraction instrument in the invention in an initial state.
Figure 9:
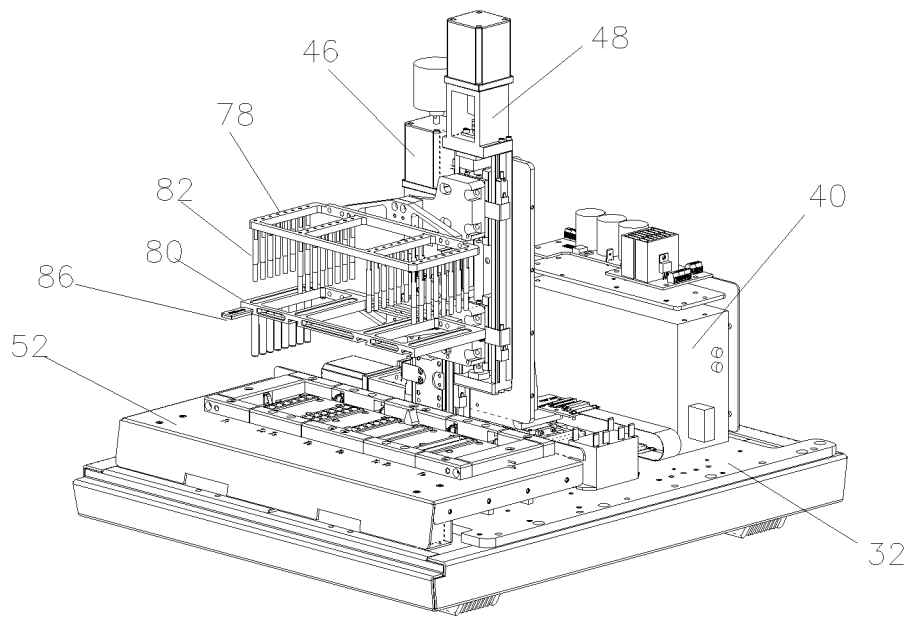
FIG. 9, similar to FIG. 8, is a schematic diagram showing the nucleic acid extraction instrument in the invention after magnetic bar sleeves are inserted.
Figure 10:
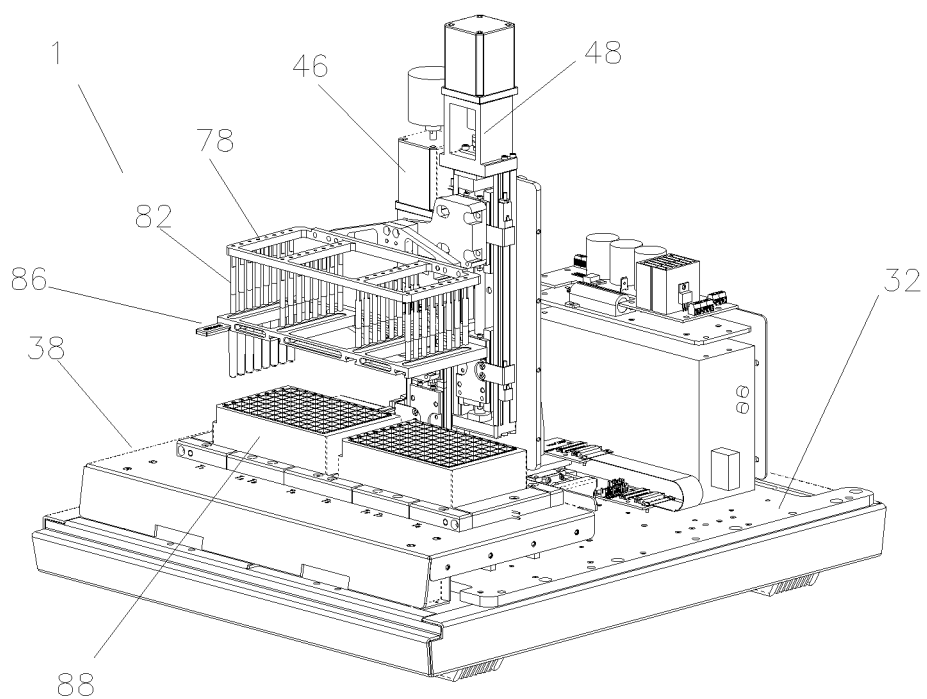
FIG. 10, similar to FIG. 9, is a schematic diagram showing the nucleic acid extraction instrument in the invention after a deep well plate is placed.
Figure 11:
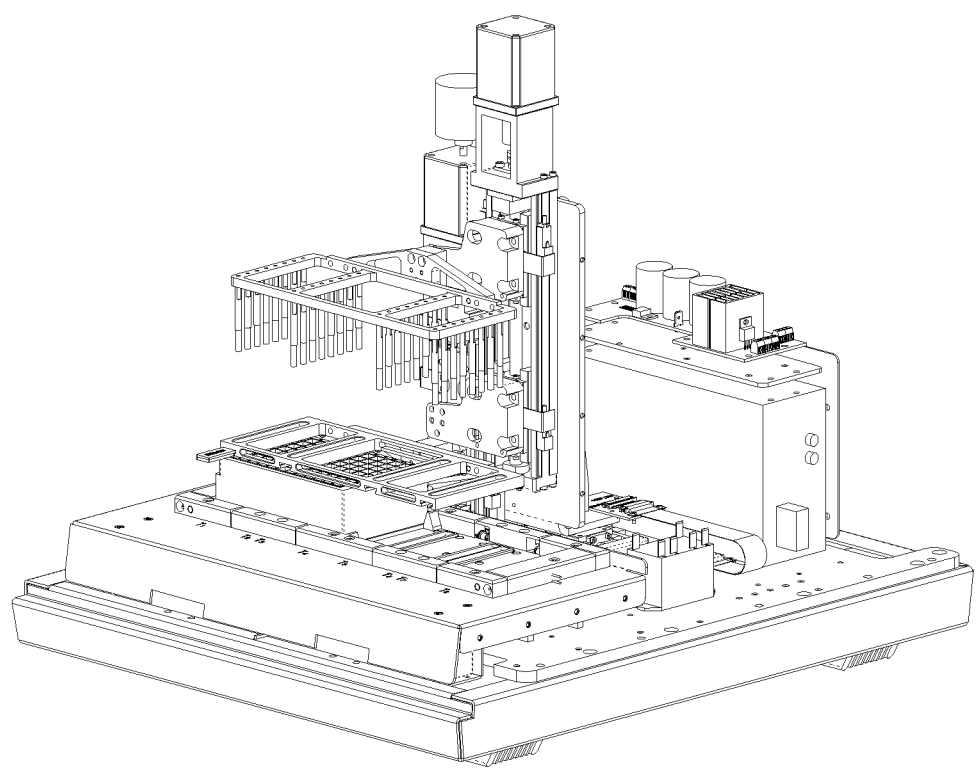
FIG. 11, similar to FIG. 10, is a schematic diagram after the magnetic bar sleeves of the nucleic acid extraction instrument in the invention enters the deep well plate.
Figure 12:
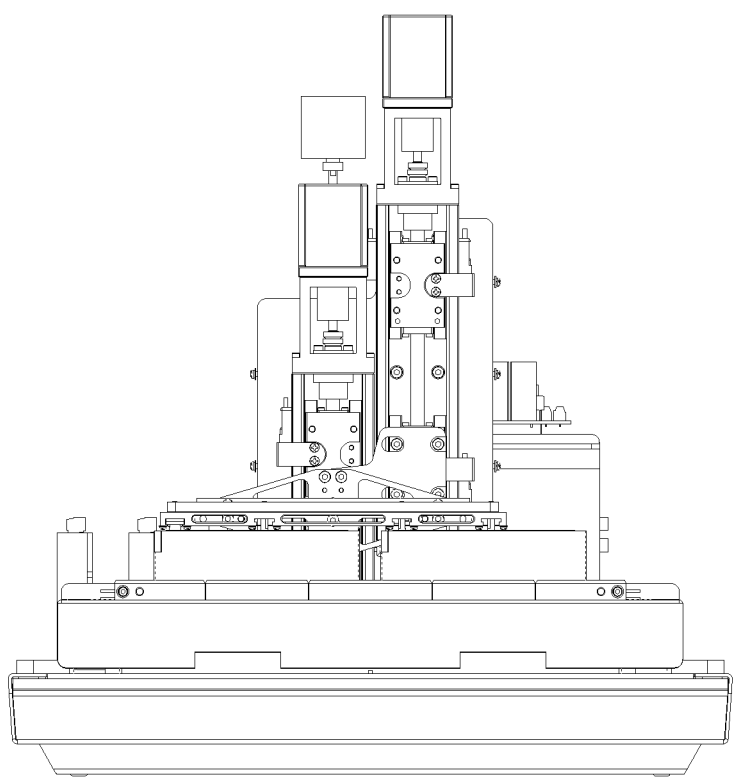
FIG. 12 is a schematic plan view when both of the magnetic bar sleeves and magnetic bars of the nucleic acid extraction instrument in the invention enter the deep well plate to be at a first position.
Figure 13:
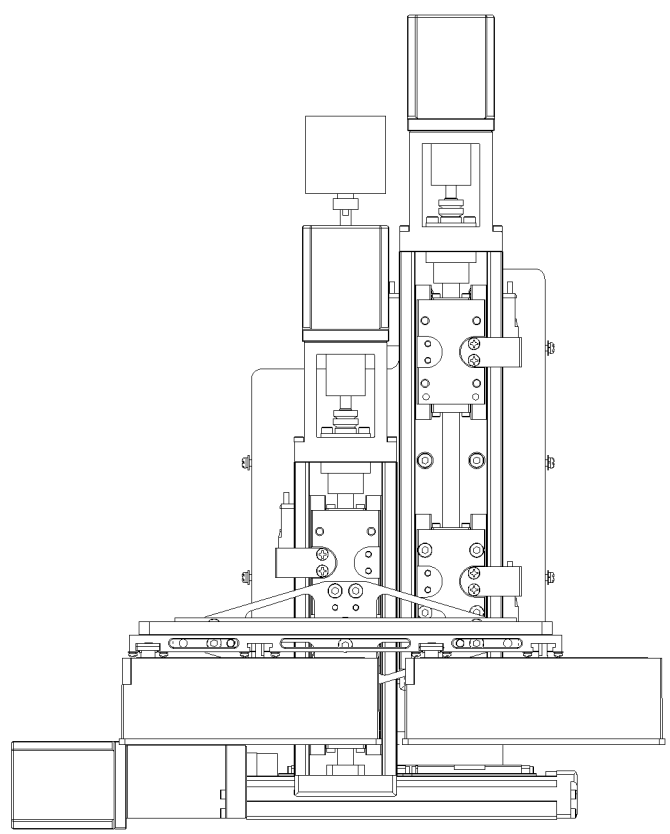
FIG. 13, similar to FIG. 12, is a schematic plan view when a first motor set drives a second motor set and a third motor set to move to a second position.
Figure 14:
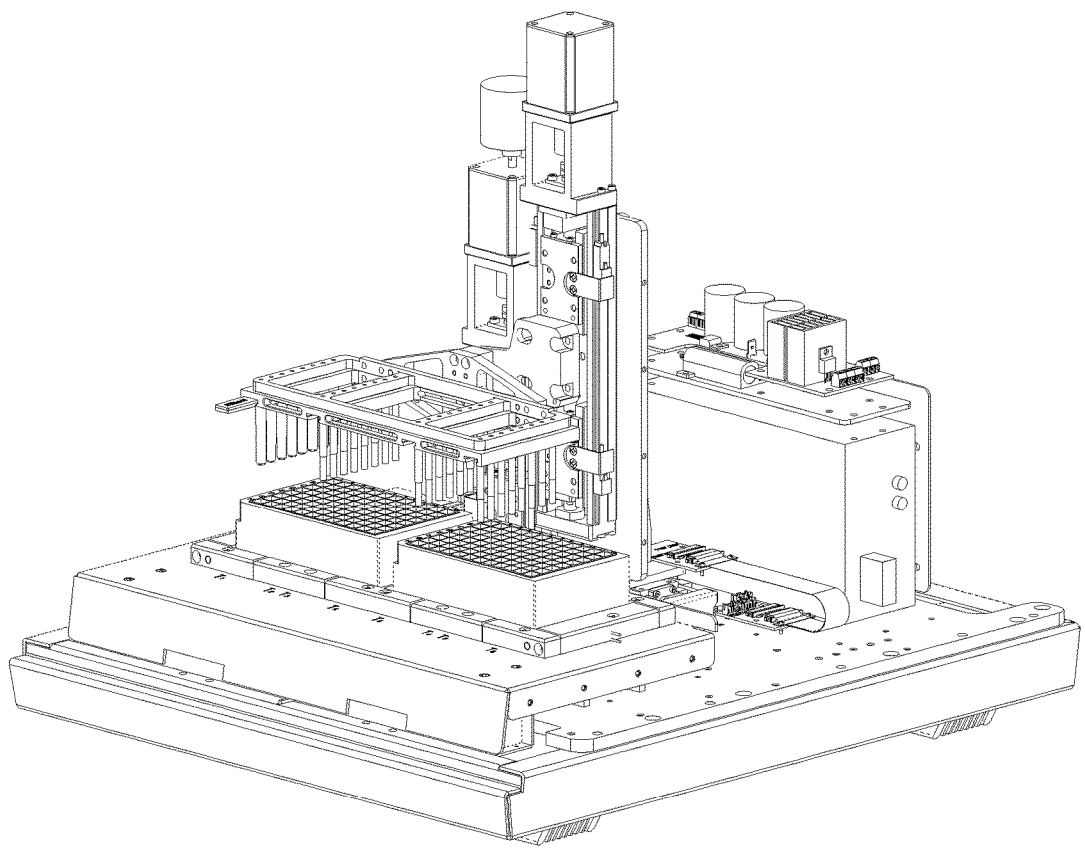
FIG. 14 is a schematic diagram after the magnetic bar sleeves and the magnetic bars of the nucleic acid extraction instrument in the invention adsorb magnetic balls and nucleic acid.
Figure 15:
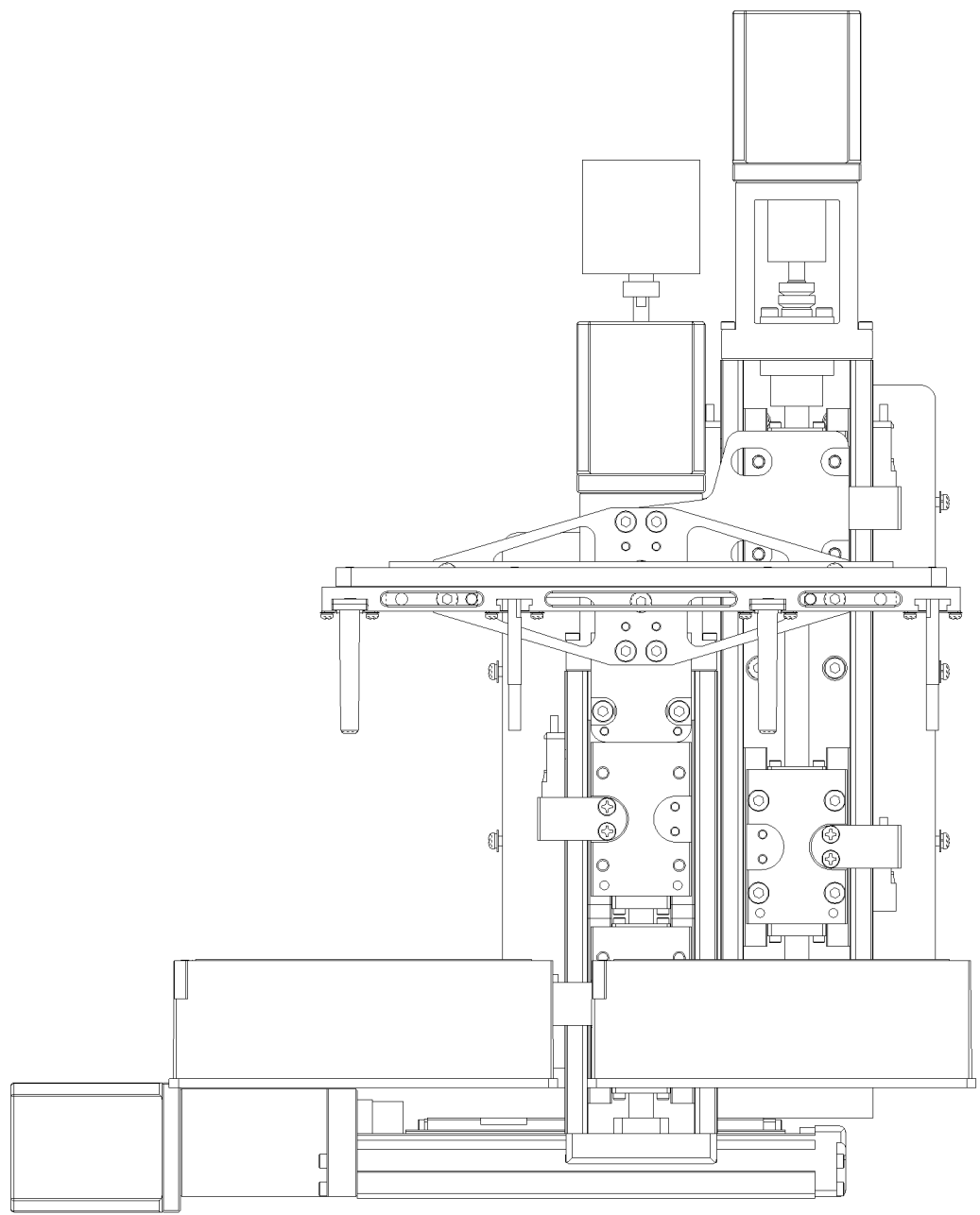
FIG. 15 is a schematic plan view when the magnetic bar sleeves and magnetic bars of the nucleic acid extraction instrument in the invention are in a moving process.
Figure 16:
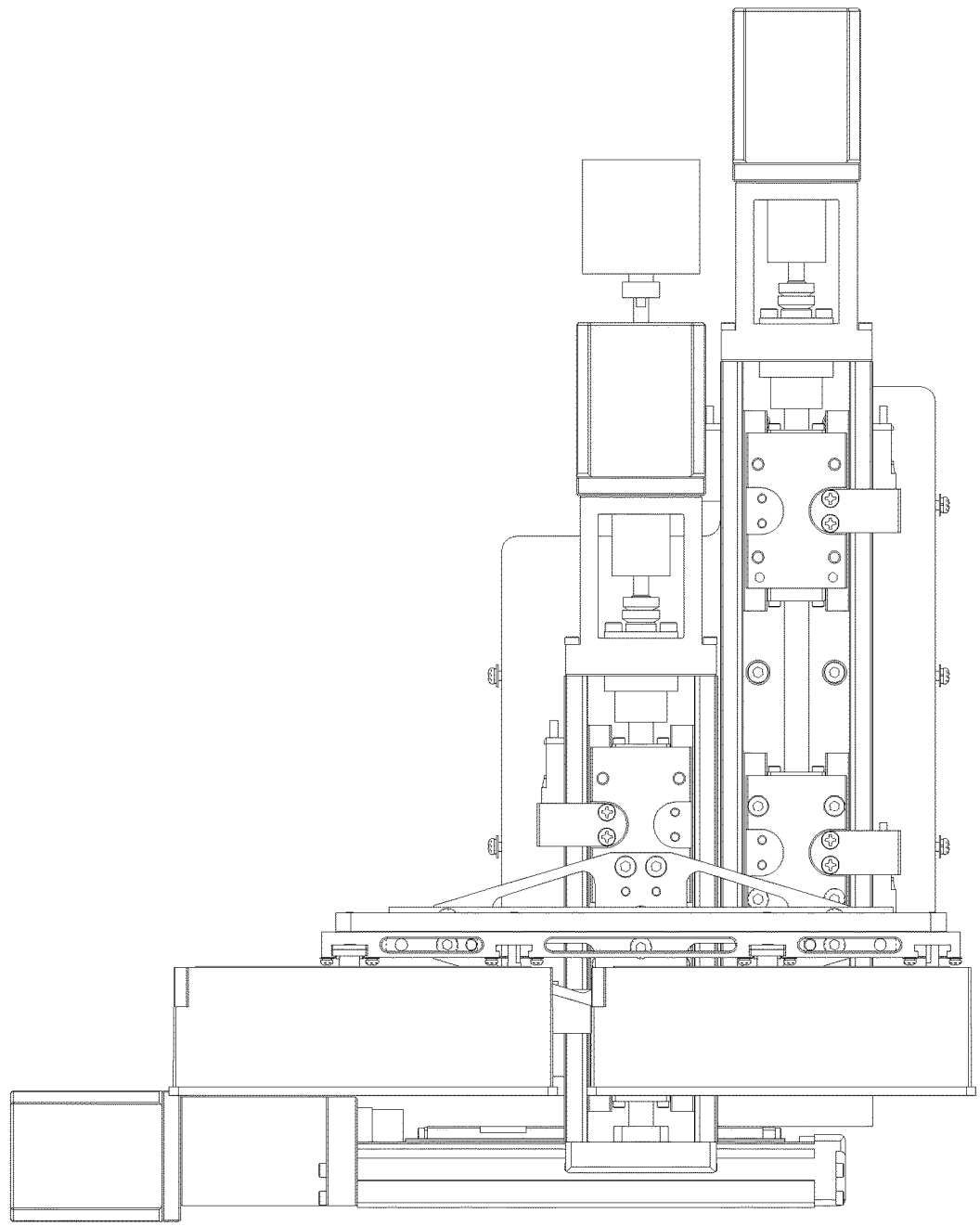
FIG. 16, similar to FIG. 13, is a schematic plan view when both of the magnetic bar sleeves and the magnetic bars enter the deep well plate to be at a second position.

As shown in FIG. 8, the nucleic acid extraction instrument in the present invention includes a magnetic bar frame 78 fixedly connected to a sliding block of the second motor set 46 and a magnetic bar sleeve frame 80 fixedly connected to a sliding block of the third motor set 48. The magnetic bar frame 78 is downward provided with a plurality of rows of magnetic bars 82, and each row has a plurality of magnetic bars (preferably 4*8 magnetic bars). The magnetic bar sleeve frame 80 is downward provided with channels 84 with a number (such as four) corresponding to the number of the rows of the magnetic bars. One magnetic bar sleeve may be inserted in each channel 84.

FIG. 8-FIG. 16 show a running process of a nucleic acid extraction instrument 1 in the present invention. When the nucleic acid extraction instrument 1 is in a starting position, the magnetic bar frame 78 is separated from the magnetic bar sleeve frame 80 and is spaced a sufficiently large distance from the operating platform 38. The nucleic acid extraction instrument 1 in the present invention sequentially runs according to the following steps. A first step: adding a sample—a deep well plate (also named as 96-well plate) in which the sample is added is placed at a specified position of the operating platform 38, and then the magnetic bar sleeves 86 are fixed to the channels 84 of the magnetic bar sleeve frame 80. A second step: lysing—the third motor set 48 is started to allow the magnetic bar sleeve frame 80 to drive the magnetic bar sleeves 86 to descend until the magnetic bar sleeves 86 enter a specified row of wells of the deep well plate 88, the third motor set 48 then drives the magnetic bar sleeve frame 80 and the magnetic bar sleeves 86 together to vibrate for a preset time according to a frequency selected from (2-100) Hz (preferably, 2 Hz, 4 Hz, 8 Hz, 16 Hz, 21 Hz, 30 Hz, 50 Hz, 80 Hz, or 100 Hz), the ends, which are far away from the magnetic bar sleeve frame 80, of the magnetic bar sleeves 86 stir a mixture of the sample, a lysing solution, and magnetic balls (placed in the wells of the deep well plate in advanced) in the wells of the deep well plate 88, so that nucleic acid in the sample is separated from the sample (that is, the nucleic acid is lysed) and adsorbed on the magnetic balls. A third step: attracting—the second motor set 46 is started and drives the magnetic bar frame 78 to descend until the magnetic bars 82 enter specified positions of the magnetic bar sleeves 86 to rest for a preset time, so that all the magnetic balls are attracted on outer surfaces of the magnetic bar sleeves 86 together with the nucleic acid lysed from the sample, and then the magnetic bar frame 78 and the magnetic bar sleeves 86 ascend together to ensure that the magnetic bar sleeves 86 and the magnetic bars 82 enter a specified row of washing wells of the deep well plate 88 for washing to remove impurities. A fourth step: eluting—the magnetic bar frame 78 and the magnetic bar sleeves 86 enter into eluting wells from the washing wells together, and the nucleic acid is released from the magnetic balls under an action of an eluting solution. A fifth step: recovering the magnetic balls—the magnetic balls attracted on the outer surfaces of the magnetic bar sleeves 86 are transferred into magnetic ball recovering wells from the eluting wells, and the magnetic bars 82 leave from the magnetic bar sleeves 86. A sixth step: discarding the magnetic balls—the magnetic bar sleeves 86 vibrate in the magnetic ball recovering wells, so that the magnetic balls all fall off from the outer surfaces of the magnetic bar sleeves 86. A seventh step: cleaning—discharging the magnetic bar sleeves 86, removing the deep well plate, and returning the instrument to the starting position. Wherein, in the lysing and eluting steps, the sample mixed solution in the deep well plate is required to be heated to reach a preset temperature range.

Figure 26:
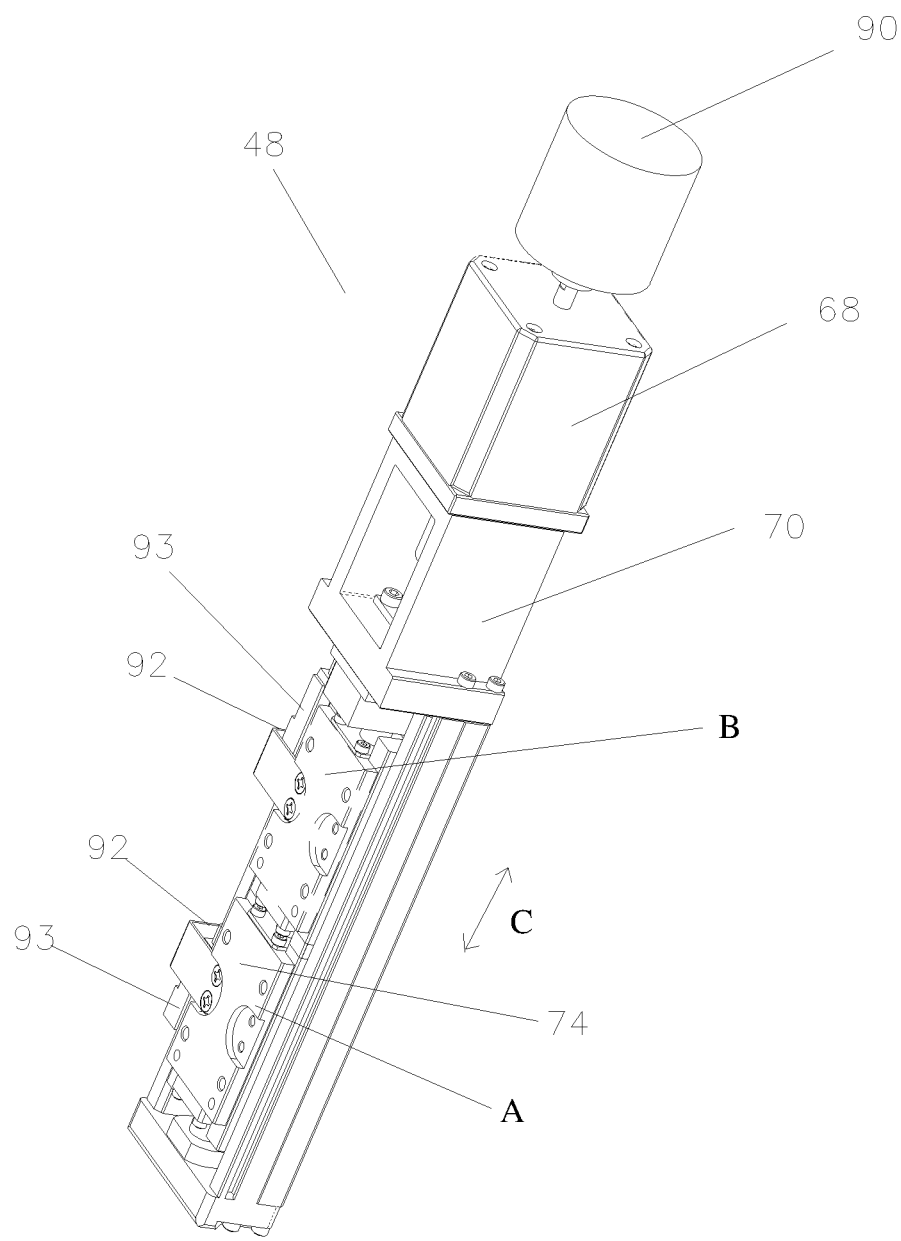
FIG. 26 is an enlarged schematic diagram a third motor set.
Figure 27:
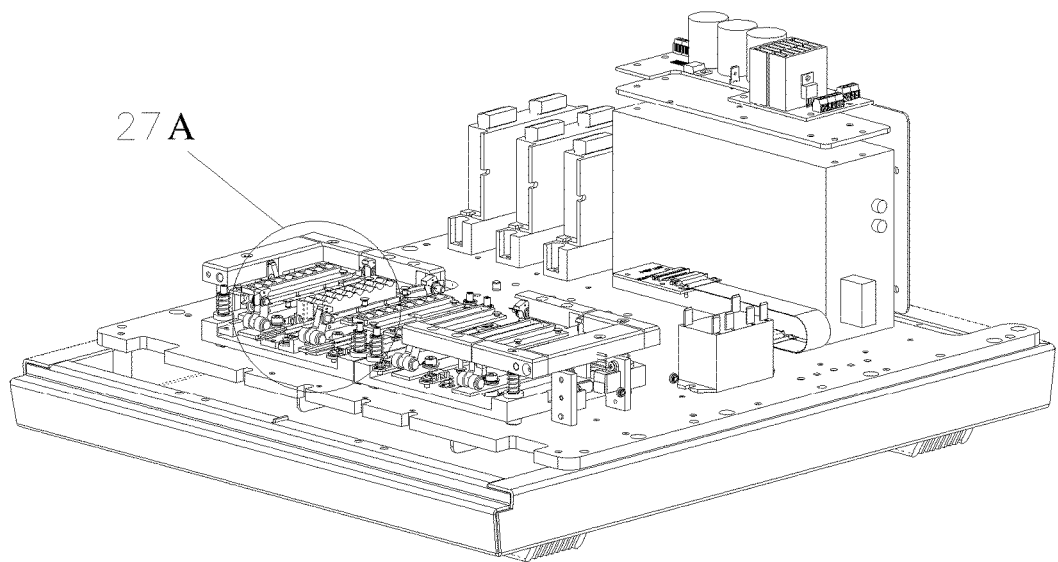
FIG. 27 is a schematic diagram showing the nucleic acid extraction instrument in the invention after partial elements are removed.
Figure 27A:
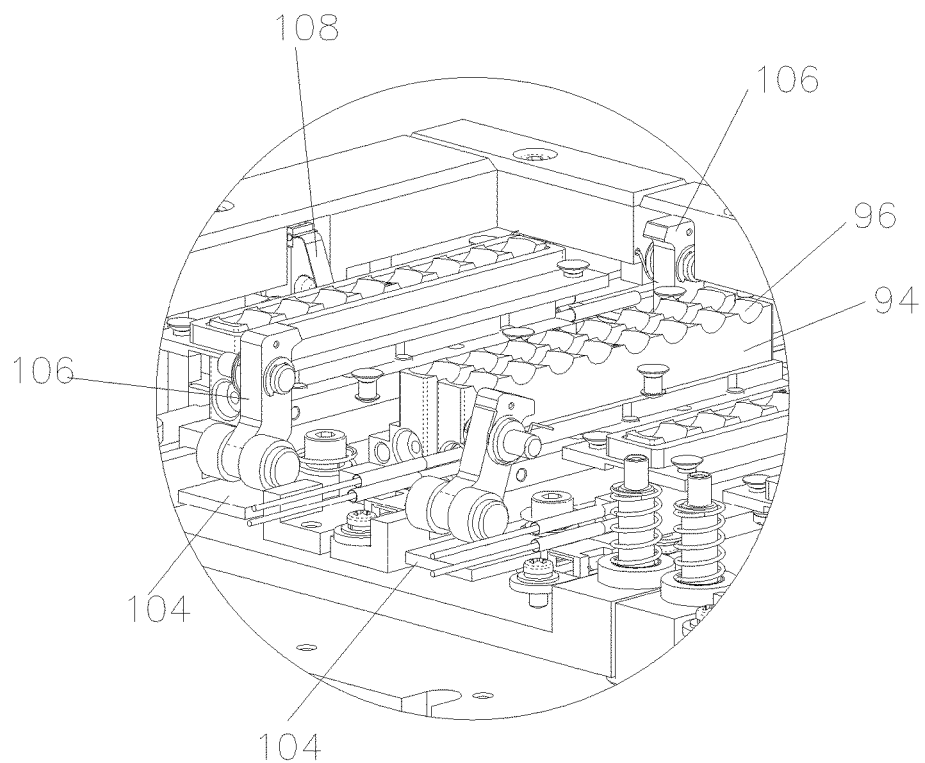
FIG. 27A is a schematic partial enlarged view of FIG. 27.

As shown in FIG. 7, FIG. 25, and FIG. 26, the first motor set 44, the second motor set 46, and the third motor set 48 are approximately identical in structures, and each adopts a step motor and a ball screw which have a high precision. A repeating precision (that is, a displacement error made by each cycle) of the step motors adopted by the present invention is less than 0.02 mm. As described above, the first motor set 44 is used for driving the second motor set 46 and the third motor set 48 to move between the first position and the second position according to a preset program. The second motor set 46 is used for driving the magnetic bar frame 78 to move upward or downward. The third motor set 48 is used driving the magnetic bar sleeve frame 80 to move upward or downward and vibrate. Because the third motor set 48 needs to drive the magnetic bar sleeve frame 80 to vibrate at a high frequency, the higher the vibrating frequency is, the larger the impulse of the inertia generated by the mass of the magnetic bar sleeve frame per se to the third motor set 48 is, and the larger the interference is. Therefore, the probability of out of step of the motor (under one pulse, the case that the displacement error output by the step motor exceeds a design value is called as the out of step of the motor) is also larger. To avoid the motor to step out, a coder 90 is disposed at the third motor set 48 according to the present invention. The coder 90 includes a component for monitoring a running condition of the step motor and a component for sending a correction instruction to the step motor. When an error between a stroke generated after the step motor receives one pulse and a pre-designed value is greater than a preset value (such as 1.25 micrometers), the coder sends one correction instruction to timely correct the stroke output by the step motor according to each pulse, thereby avoiding the out of step of the motor in advance and improving the precision that the third motor set 48 drives the magnetic bar sleeve frame 80 to vibrate.

In addition to the running precision of the motor sets, factors influencing a movement precision of the magnetic bar sleeve frame 80 and the magnetic bar frame 78 further include an initial positioning precision of the magnetic bar sleeve frame 80 and the magnetic bar frame 78 and a position precision of the maximal stroke. As such, a technical solution adopted by the present invention is as follows: a photoinduction arm 92 is fixed at an outer side of the sliding block 74 of each motor set, and a photocoupling sensor 93 is respectively disposed at an initial position and a maximal stroke position of the sliding block 74. The photocoupling sensor 93 monitors the position of the sliding block 74 by detecting the position of the photoinduction arm 92. Therefore, after the photocoupling sensor 93 is adopted, the first motor set 44 can accurately control the positions of the second motor set and the third motor set (that is, the magnetic bar sleeve frame 80 and the magnetic bar frame 78) corresponding to the positions where lysing, washing, eluting, and recovering of the magnetic balls are performed in the deep well plate 88; and the second motor set and the third motor set can accurately control the lowest position and the highest position of the magnetic bar sleeve frame 80 and the magnetic bar frame 78.

Figure 17:
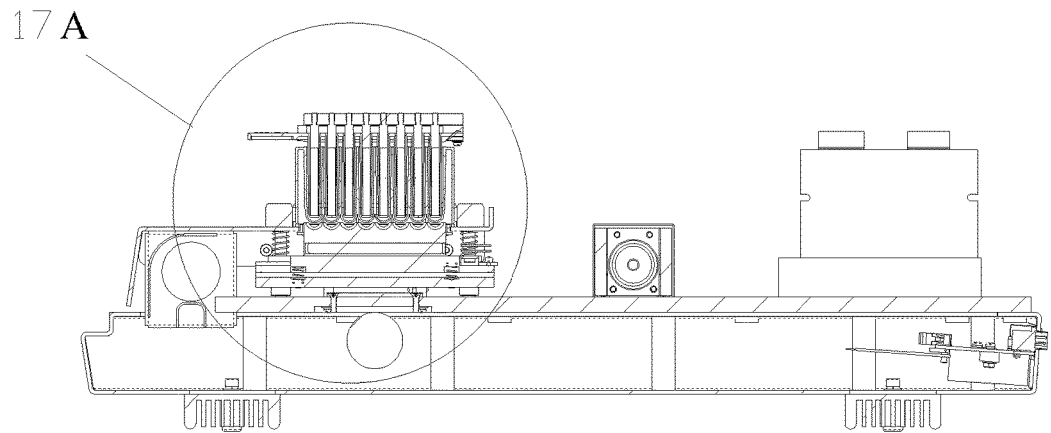
FIG. 17 is a schematic plan view of an operating platform.
Figure 17A:
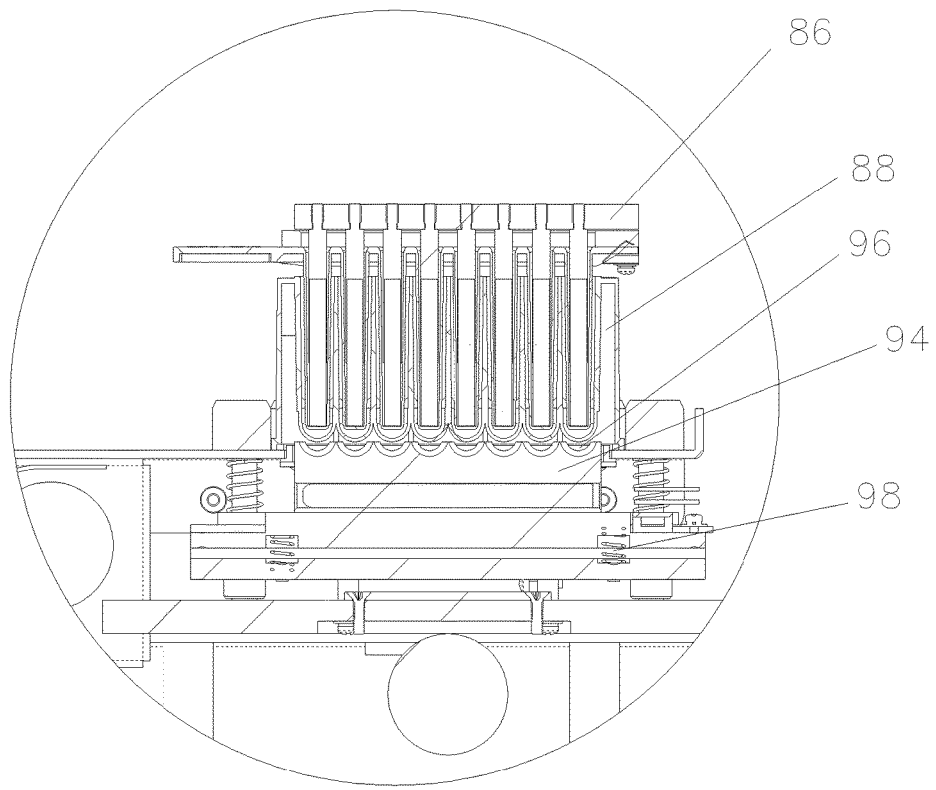
FIG. 17A is a partial enlarged view of a marked part in FIG. 17.

As shown in FIG. 17 and FIG. 17A, a plurality of rows of movable heating plates 94 is disposed on the operating platform 38. Each row of the heating plates 94 includes a plurality of heating well walls 96 closely matching the shape of the bottom of the deep well plate 88. The heating plates 94 are preferably made of a metal material, a heating component (unmarked) such as a resistance wire is disposed inside the heating plates 94 in a penetrating manner, and a heat insulating component (unmarked) is disposed around the heating plates 94. A plurality of mutually independent compression springs 98 is disposed under the heating plates 94 to promote all the heating well walls 96 of the heating plates 94 to attach to the bottom of the deep well plate 88 more uniformly, thereby making each well heated more uniformly. This greatly improves the consistency of lysing and eluting efficiencies of the samples in respective wells in the deep well plate 88, thereby greatly reducing an error of nucleic acid extraction efficiencies in respective wells.

As shown in FIG. 23, FIG. 27, FIG. 27A, and FIG. 30, the operating platform 38 includes at least one set of clamping tools for automatically clamping and releasing the deep well plate 88 placed on the operating platform 38. The clamping tools includes motors 100 (the number of the motors corresponds to the number of the deep well plates) positioned below the bottom plate 32 (that is, a back face of the operating platform 38), a supporting portion 104 positioned inside the operating platform 38, a plurality of clamping arms 106, and a microswitch 108. The clamping arms 106 include a shaft 105, an up-down movement of the supporting portion pushes the clamping arms 106 to rotate around the shaft 105, clamping heads 107 of the clamping arms tightly clamp or release the deep well plate 88. The motor 100 includes a cam 102. When the motor 100 is started, the cam 102 pushes the supporting portion 104 to move upward or downward. The supporting portion 104 further pushes the clamping arms 106 to rotate clockwise or anticlockwise according to a lever principle, and the clamping arms 106 tightly clamp or release outer walls of the deep well plate 88. Torsional springs (unmarked) are disposed at the clamping arms, and when no deep well plate 88 is placed on the operating platform 38, the torsional springs make the clamping arms keep a releasing state to reduce the obstruction of placing the deep well plate 88 onto the operating platform 38.

Figure 18:
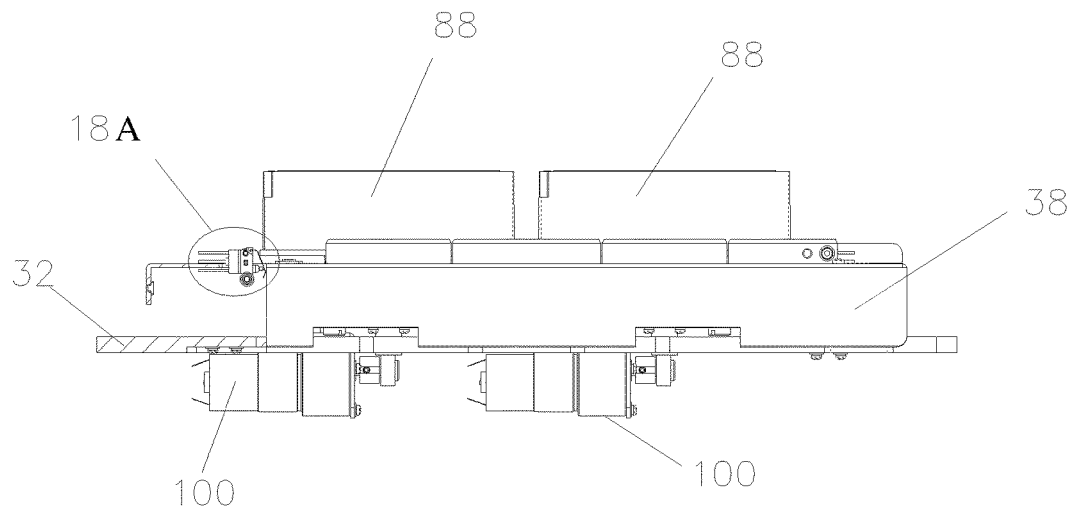
FIG. 18 is a schematic plan view of the operating platform in another perspective.
Figure 18A:
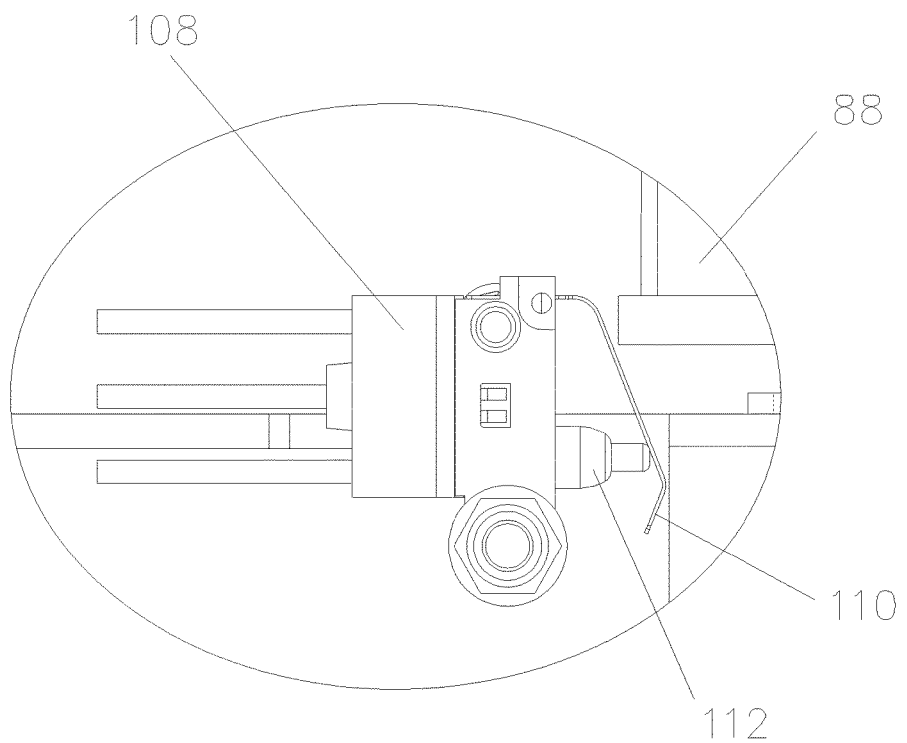
FIG. 18A is a partial enlarged view of a marked part in FIG. 18.
Figure 19:
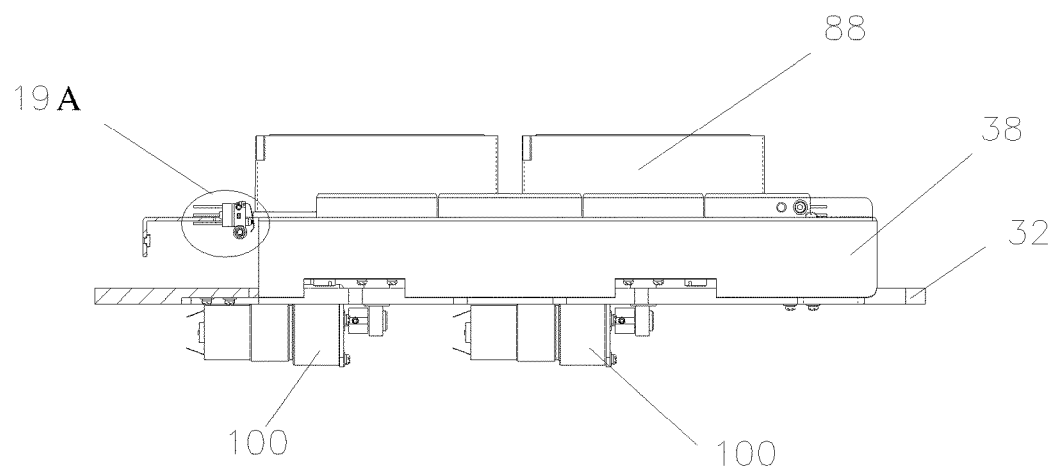
FIG. 19 is a schematic plan view similar to FIG. 18, wherein a switch is in a triggering state.
Figure 19A:
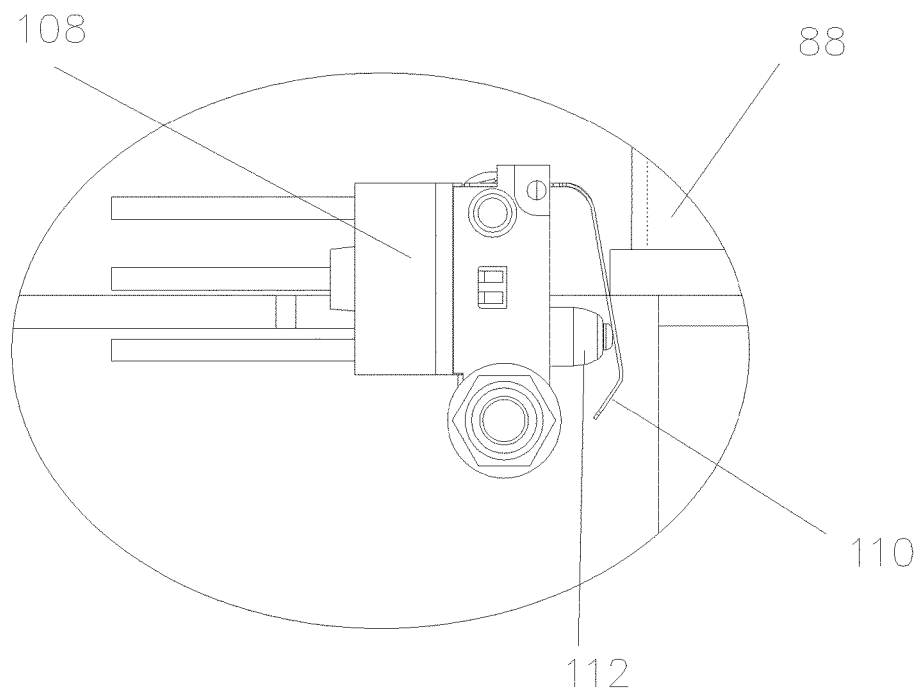
FIG. 19A is a partial enlarged view of a marked part in FIG. 19.
Figure 20:
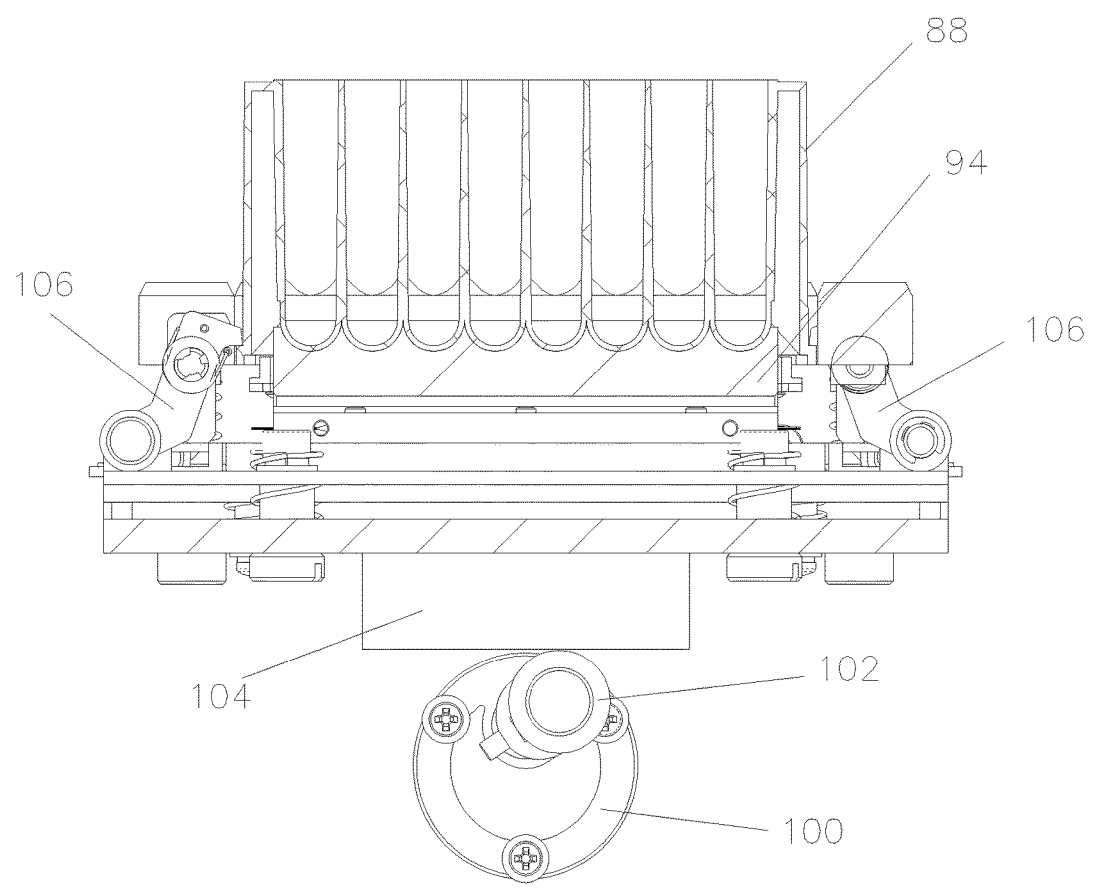
FIG. 20-FIG. 23 are working schematic diagrams of clamping tools.
Figure 21:
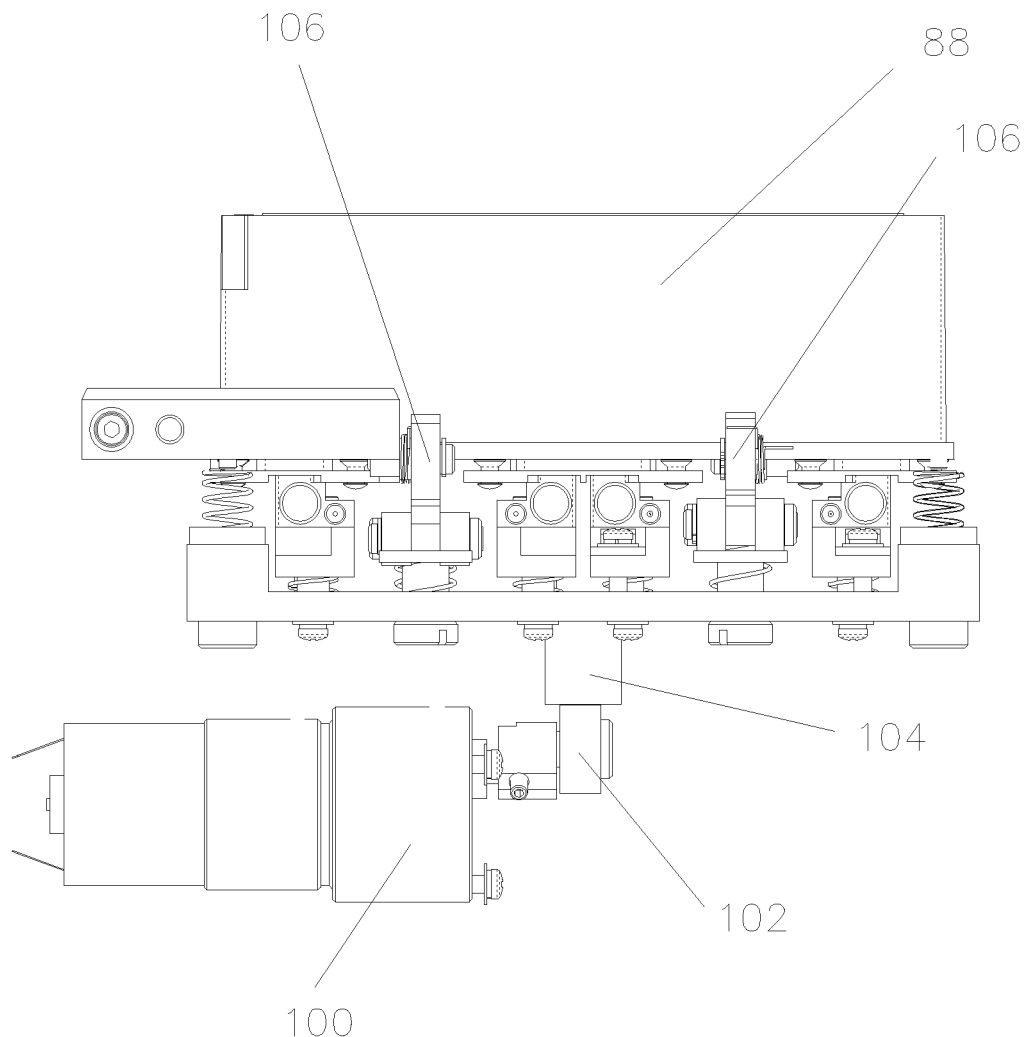
Figure 22:
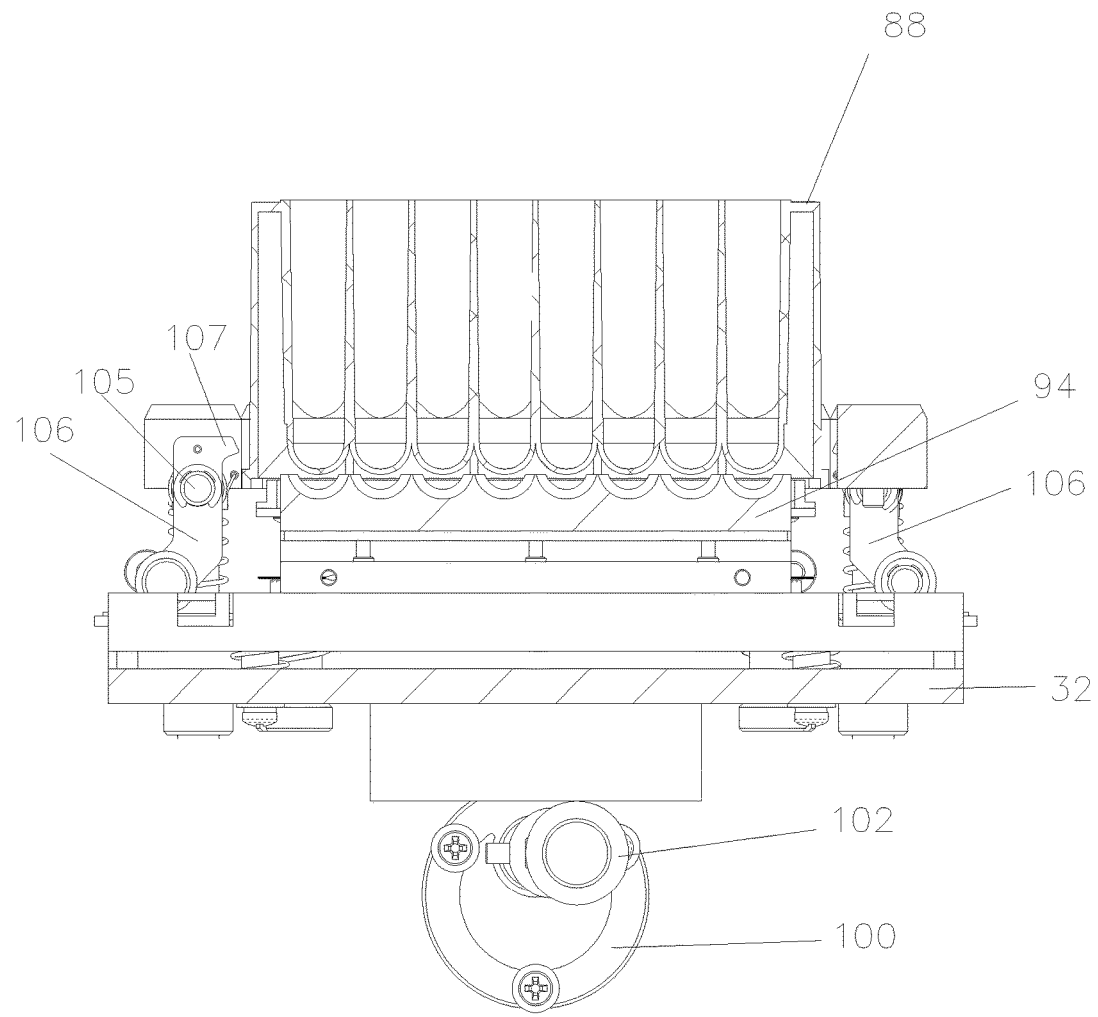
Figure 23:
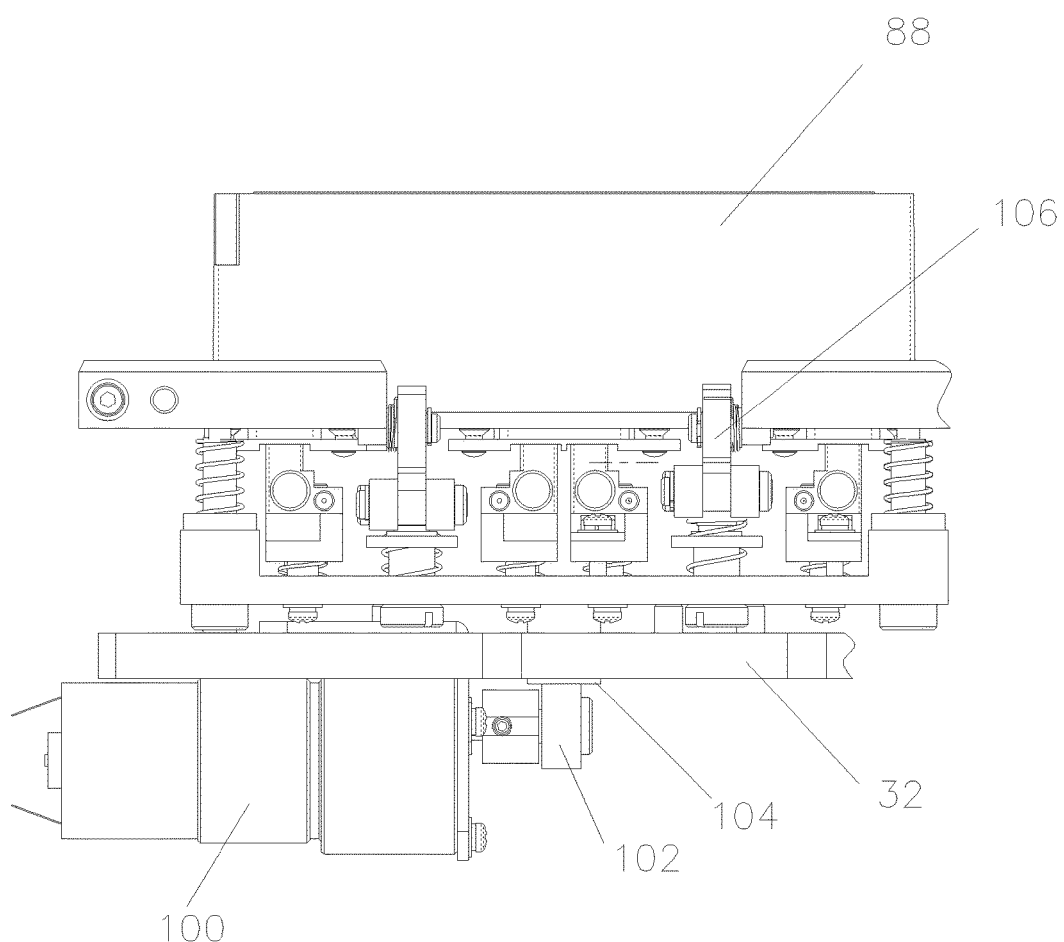

As shown in FIG. 18, FIG. 18A, FIG. 19, FIG. 19A, FIG. 20, FIG. 21, FIG. 22, FIG. 23, FIG. 28, and FIG. 28A, the microswitch 108 is positioned near one end of the operating platform 38. The microswitch 108 includes a spring leaf 110 and a button switch 112. FIG. 18A is a view showing that the microswitch is in a turning-off state, and FIG. 19A is a view showing that the microswitch is in a turning-on state. When the deep well plate 88 is placed to a predetermined position of the operating platform 38, side walls of the deep well plate 88 push the spring leaf 110 to compress the button switch 112, thereby turning on the microswitch 108 to start the motor 100 to work. The motor 100 drives the cam 102 to push the supporting portion 104 to move upward. The supporting portion 104 further pushes the clamping arms 106 to rotate according to the lever principle to make the clamping arms 106 tightly clamp the outer walls of the deep well plate 88, thereby precisely fixing the deep well plate 88 to a position on the operating platform 38. When there is a need for removing the deep well plate 88 from the operating platform 38 after the whole process of extracting the nucleic acid finishes, the operator sends an instruction of releasing the deep well plate 88 by the instrumental panel 22. The motor 100 drives the cam 102 to rotate, and the supporting portion 104 moves downward under the action of springs and self-gravity. Under the action of the torsional springs, the clamping arms 106 reversely rotate to return to a state of releasing the deep well plate 88 and do not exert a clamping force to the deep well plate 88. Therefore, the operator can easily remove the deep well plate 88 from the operating platform 38.

Figure 28:
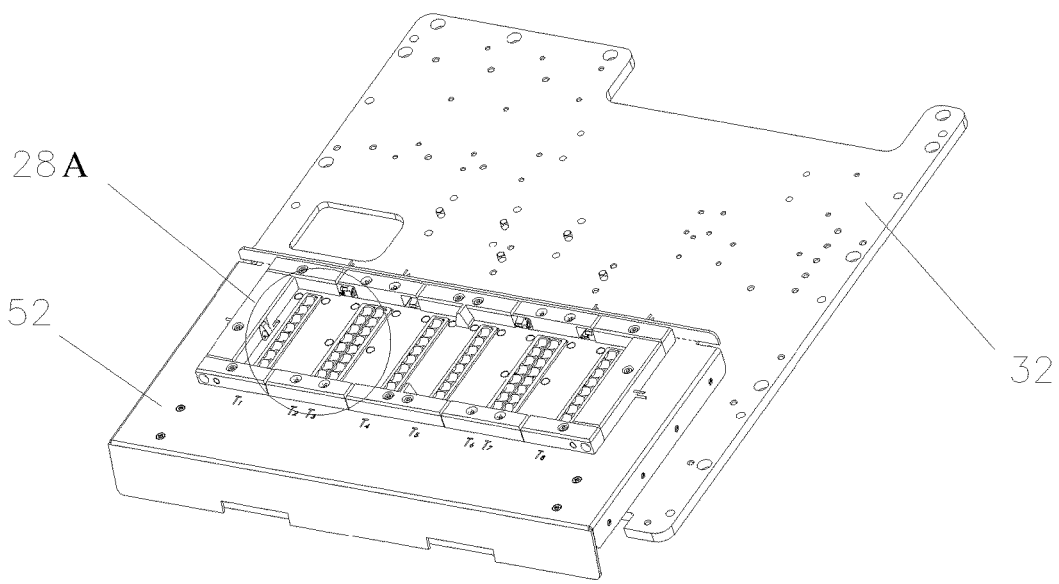
FIG. 28 is a schematic diagram of a bottom plate and the operating platform of a nucleic acid extraction instrument in the invention.
Figure 28A:
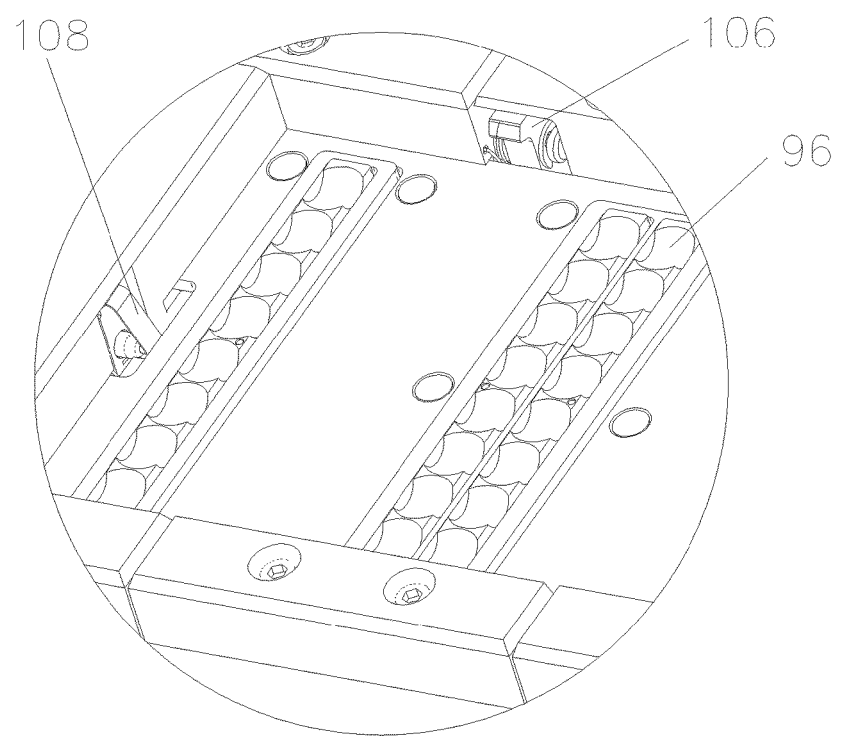
FIG. 28A is a schematic partial enlarged view of FIG. 28.
Figure 29:
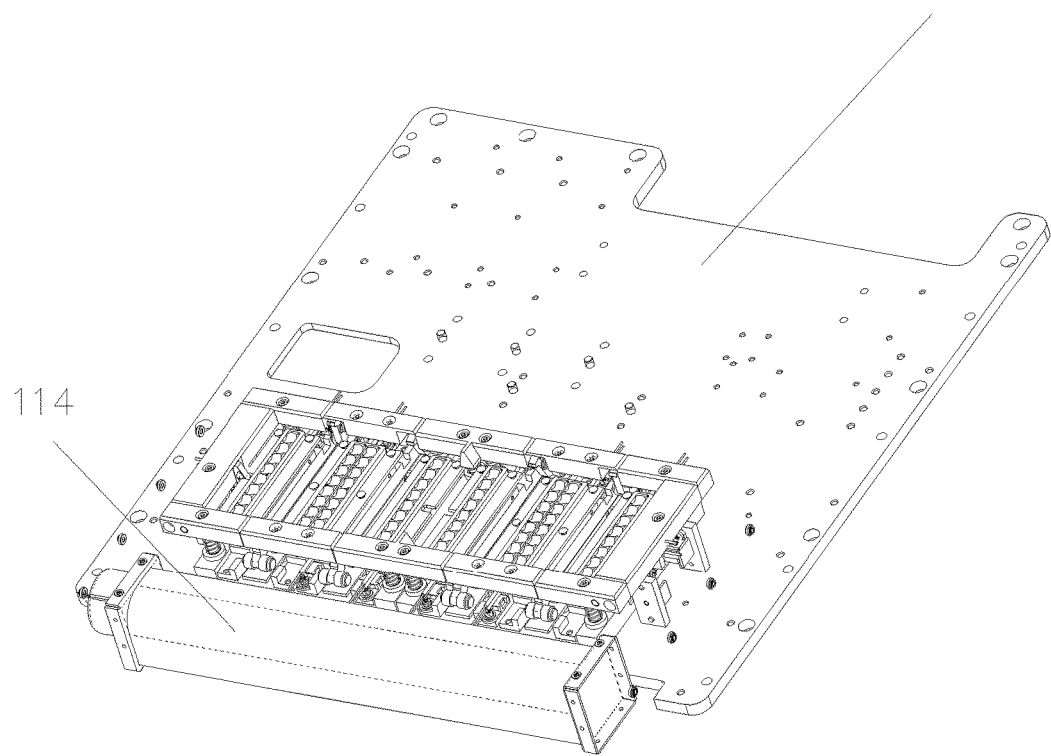
FIG. 29 is a schematic diagram of FIG. 28 after an operating panel is removed.
Figure 30:
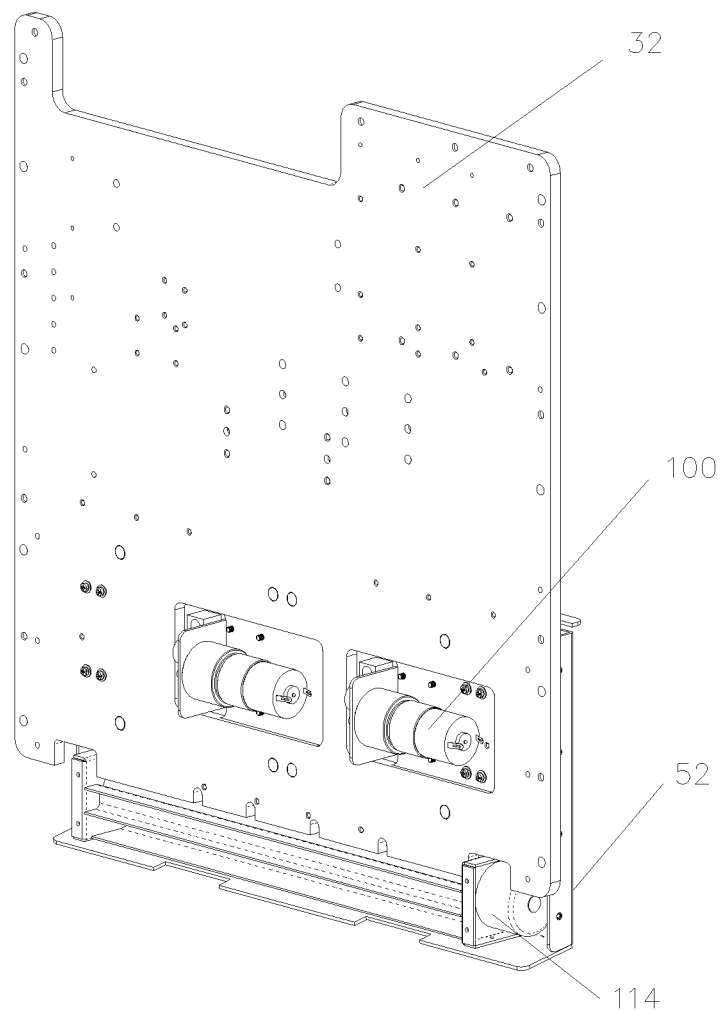
FIG. 30 is a schematic diagram of a bottom plate from bottom to top.
Figure 31:
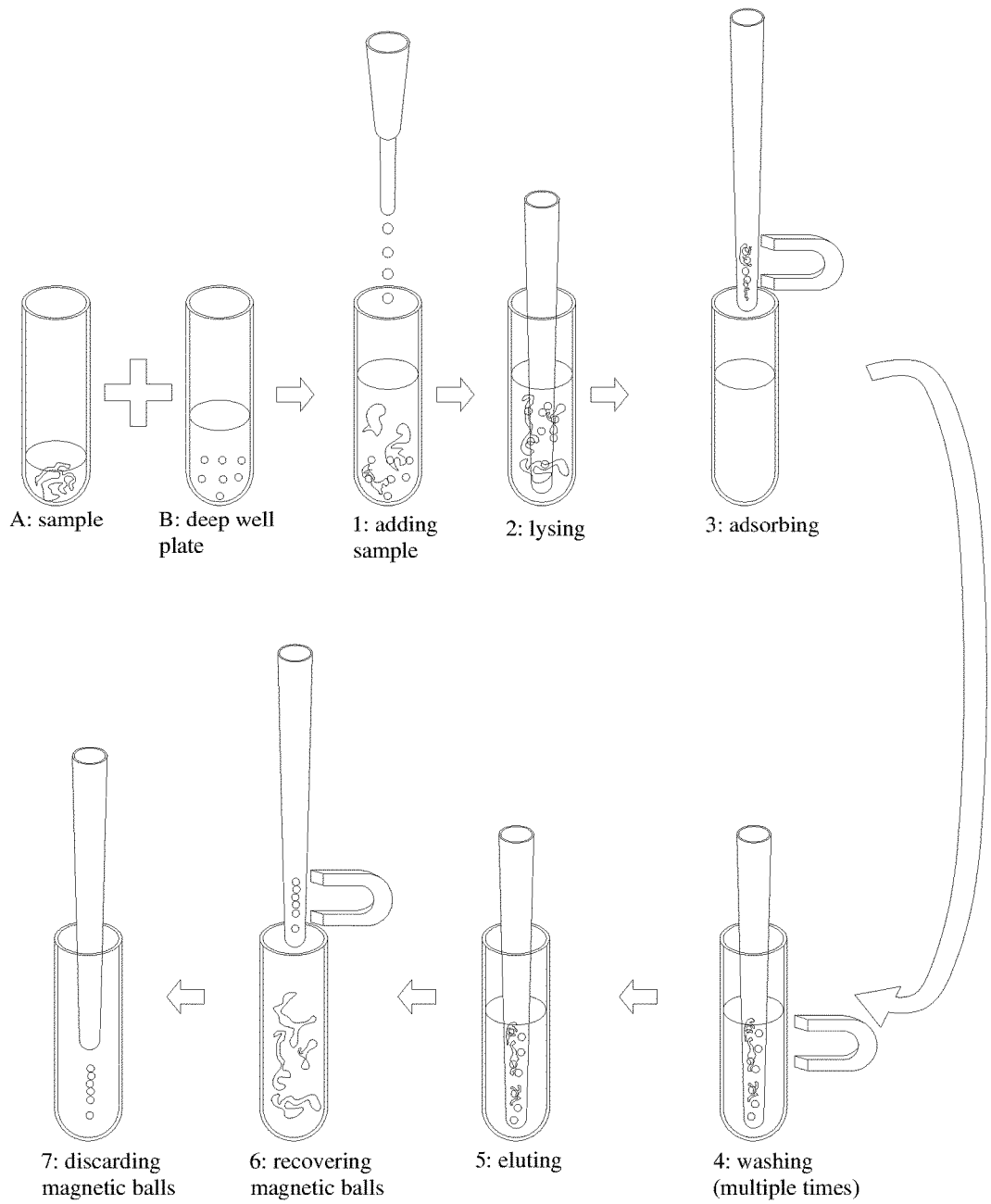
FIG. 31 is a principle schematic diagram of the invention.
Figure 32:
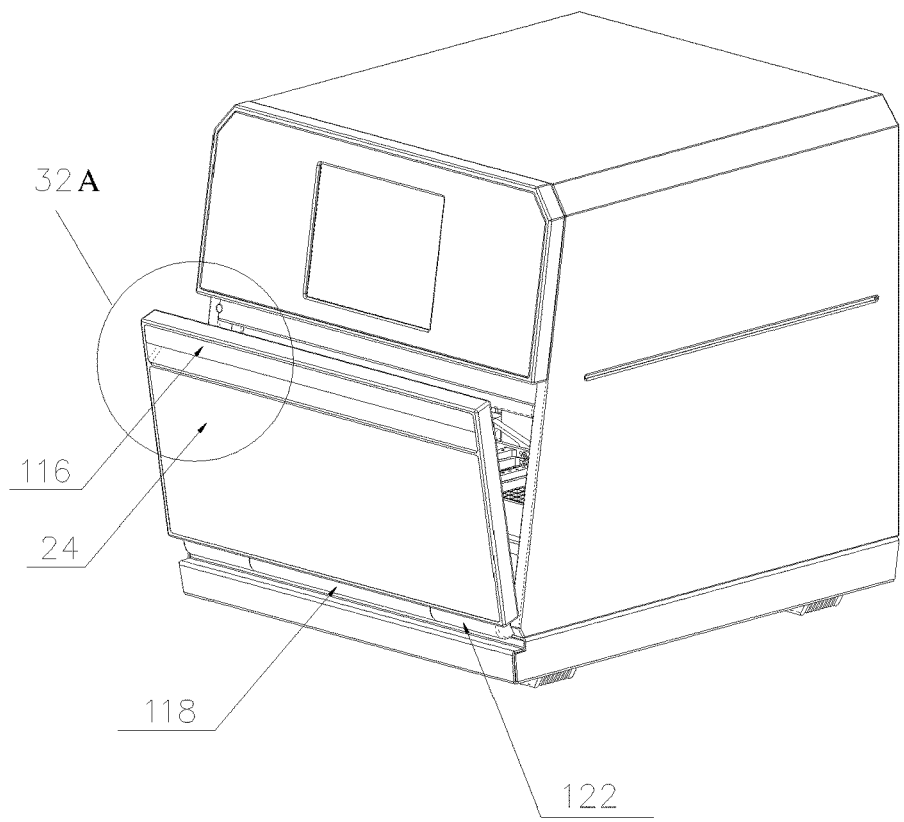
FIG. 32 is a schematic diagram of a door of the nucleic acid extraction instrument in the invention.
Figure 32A:
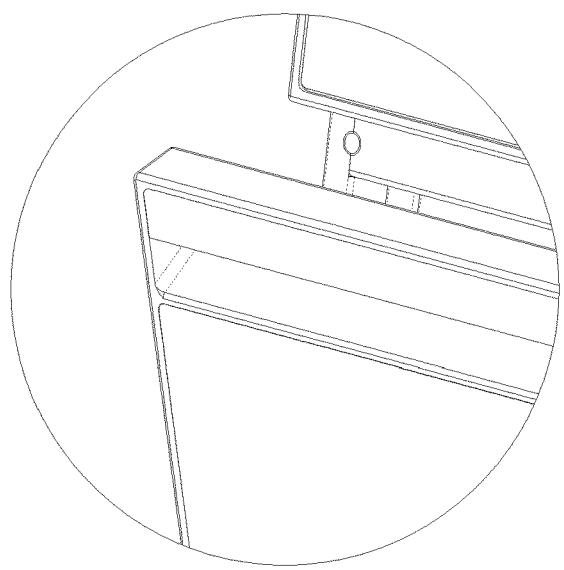
FIG. 32A is a schematic partial enlarged view of FIG. 32.
Figure 33:
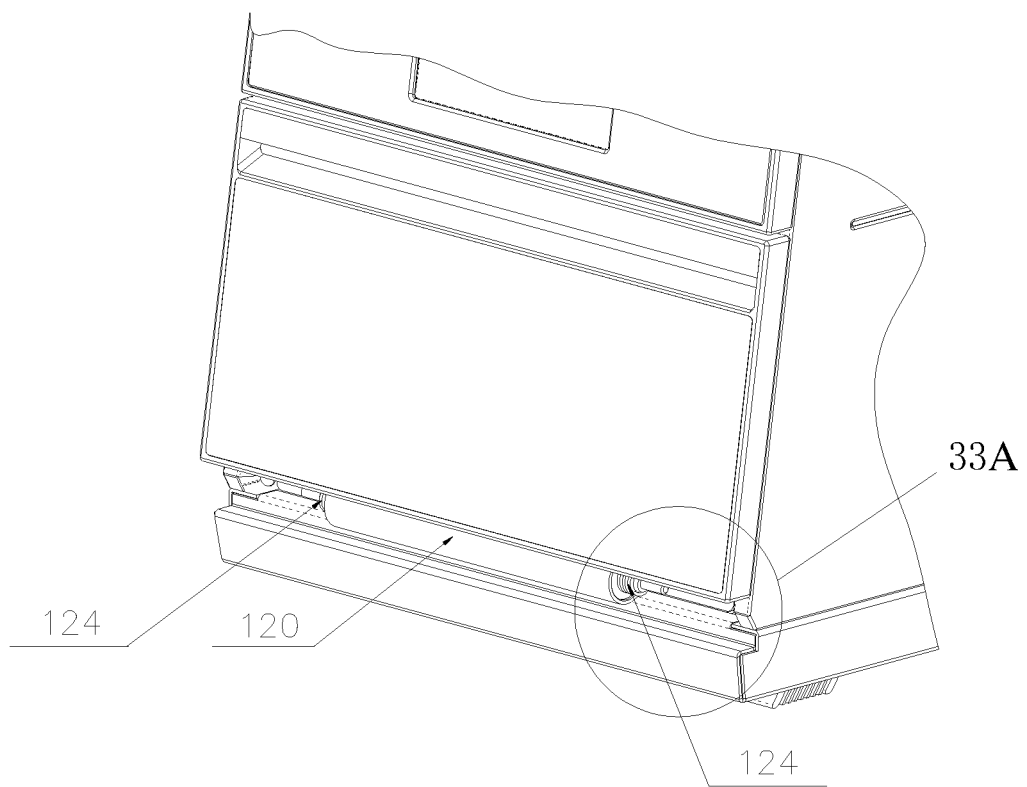
FIG. 33 is a schematic partial enlarged view of the door of the nucleic acid extraction instrument in the invention.
Figure 33A:
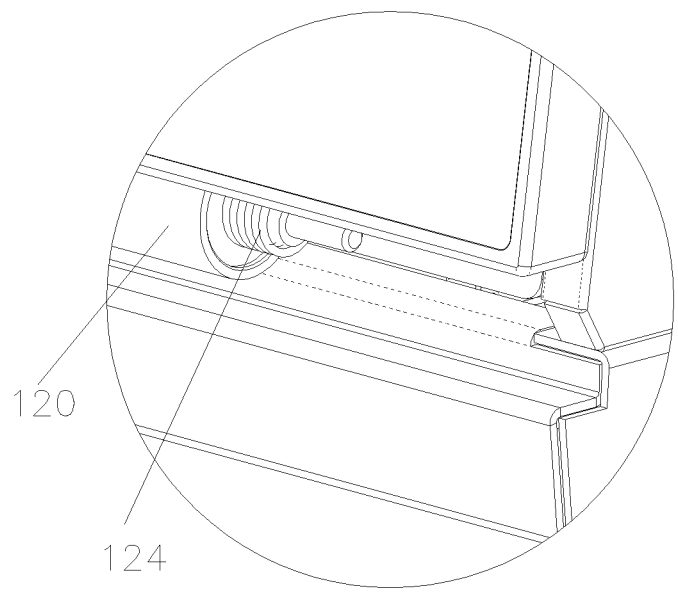
FIG. 33A is a schematic partial enlarged view of FIG. 33.

As shown in FIG. 28, FIG. 29 and FIG. 30, a cross flow fan 114 used for radiating heat to outside of the instrument is disposed at the end, close to the instrumental panel 22, of the operating platform 38. The cross flow fan 114 is hidden below the operating panel 52 of the operating platform 38. An air outlet of the cross flow fan 114 is positioned in the bottom of the nucleic acid extraction instrument of the present invention.

As shown in FIG. 1, FIG. 2 and FIG. 3, the instrumental main body 30 of the nucleic acid extraction instrument in the present invention is basically enclosed by the base 10 and the outer housing 20, while the bottom of the base 10 is provided with an air outlet for the cross flow fan 114. The nucleic acid extraction instrument of the present invention is further provided with the inner housing 34 and the operating panel 52. The inner housing 34 and the operating panel 52 basically limit the deep well plate 88 in a relatively closed space. The above structure design is very beneficial to preventing an external environment from influencing the cleanness inside the instrument.

As shown in FIG. 32, FIG. 32A, FIG. 33, and FIG. 33A, the door 24 of the nucleic acid extraction instrument 1 in the present invention includes a door handle 116 and a door shaft 118. Wherein, the outer housing 20 is provided with a permanent magnetic block (not illustrated) at a position corresponding to the door handle 116, and when the door 24 is closed, the permanent magnetic block attracts the door handle 116, thereby making the door 24 kept in a closed state. The door shaft 118 includes a door middle shaft 120 fixed to the base 10 and door shaft sleeves 122 fixed to two ends of the bottom of the door 24. Two ends of the door middle shaft 120 are assembled into the door shaft sleeves 122, respectively, and door shaft torsional springs 124 are disposed at the positions where the door middle shaft 120 is joined with the door shaft sleeves 122. The door shaft torsional springs 124 enable joints between the door middle shaft 120 and the door shaft sleeves 122 to keep having a certain damping coefficient, thereby increasing a hand feeling when the door 24 is opened or closed and improving a pleasant feeling of the operator.

Figure 34:
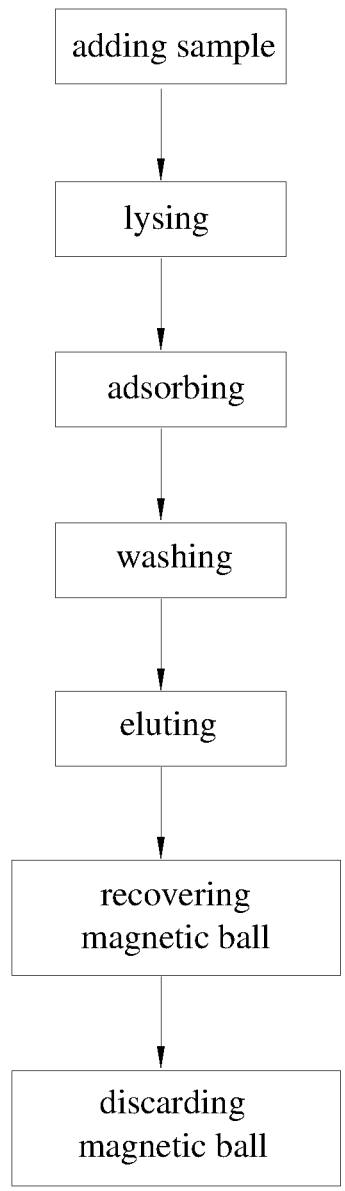
FIG. 34 is a schematic diagram showing an operating process of the nucleic acid extraction instrument in the invention.

FIG. 34 shows a working principle and steps of the nucleic acid extraction instrument in the present invention. A first step: adding a sample (such as whole blood) into the deep well plate. A second step: heating and lysing the sample under a mechanical vibration of the magnetic bar sleeves. A third step: making the magnetic bars enter into the magnetic bar sleeves and adsorbing the magnetic balls and nucleic acid. A fourth step: washing away the impurities under an action of the washing solution. A fifth step: eluting the nucleic acid from the magnetic bar sleeves under an action of an eluting solution. A sixth step: recovering the magnetic balls. A seventh step: removing the magnetic bars from the magnetic bar sleeves and making the magnetic balls fall off from the magnetic bar sleeves under an action of the mechanical vibration of the magnetic bar sleeves and fall into the magnetic ball recovering wells.

Figure 35:
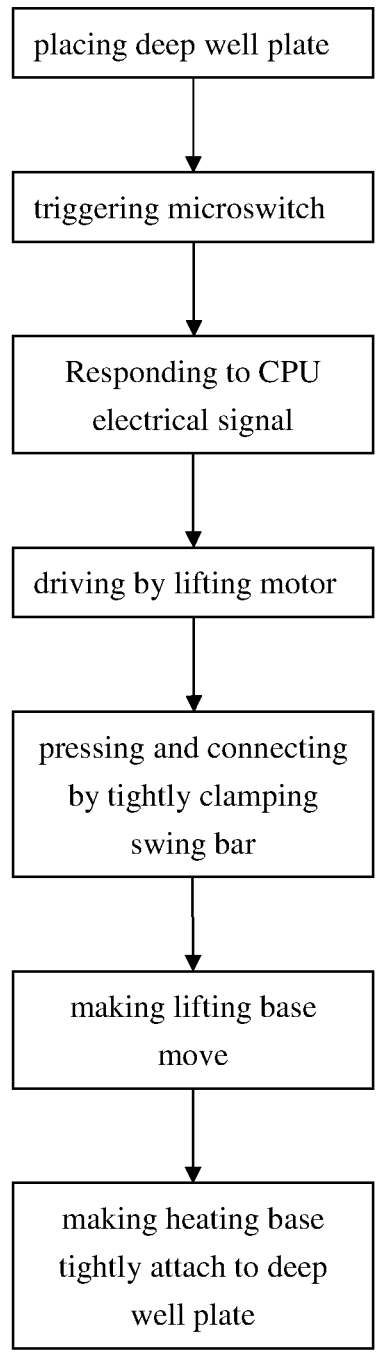
FIG. 35 is a schematic diagram when the deep well plate is tightly clamped and heated by the nucleic acid extraction instrument in the invention.

FIG. 35 shows steps for fixing the deep well plate and heating the sample by the nucleic acid extraction instrument in the present invention. A first step: placing the deep well plate. A second step: triggering the microswitch. A third step: responding to a CPU signal. A fourth step: starting the motor. A fifth step: moving the supporting portion upward. A sixth step: tightly clamping by the clamping arms. A seventh step: making the heating plates tightly attach to the deep well plate.

That a description that an element A is fixed to another element B or the like described in this patent application (including the specification and claims of the patent application) refers to that the element A is directly or indirectly fixed to another element B, including two cases that the element A and the another element B are fixedly connected together in a mutual contact manner and the element A and the another element B are not mutually in contact but are fixedly connected together by a third element. Broadly speaking, all cases that the element A and another element B cannot relatively move belong to the scope that the element A is fixed to another element B which is described in this patent application.

The content disclosed by the patent application is a merely limited record of the detailed description of the present invention, and any limited improvements performed according to the content disclosed by this patent application without making any inventive work all belong to the scope of the present invention.

What is claimed is:

1. A nucleic acid extraction instrument, comprising: a base 10, an outer housing 20 connected with the base, an instrumental main body 30 positioned inside the outer housing and mounted to the base; wherein the instrumental main body comprises an operating platform 38 configured to receive a sample plate 88, wherein the sample plate comprises a rectangular array of wells, wherein the rectangular array of wells comprises at least one first row of wells configured to receive a fluid sample for nucleic acid extraction and a magnetic ball, at least one second row of wells configured to receive a washing reagent, at least one third row of wells configured to receive an elution reagent, at least one fourth row of wells configured to recover the magnetic balls, an electrical power pack 40, a main control device 42, a first motor set 44 comprising a first motor, a second motor set 46 comprising a second motor, and a third motor set 48 comprising a third motor, wherein the first motor set is operably connected to the second motor set and the third motor set to move the second motor set and the third motor set along an axis parallel to an upper surface of the sample plate, the second motor set is operably connected to a magnetic bar frame 78 to move the magnetic bar frame along an axis perpendicular to the upper surface of the sample plate, wherein a plurality of magnetic bars 82 are affixed to the magnetic bar frame at a spacing corresponding to a row of sample wells in the rectangular array, the third motor set is operably connected to a magnetic bar sleeve frame 80 to move the magnetic bar sleeve frame along an axis perpendicular to the upper surface of the sample plate, wherein a plurality of magnetic bar sleeves 86 are affixed to the magnetic bar sleeve frame at a spacing corresponding to the row of sample wells in the rectangular array, and the main control device is configured to electronically control the first, second, and third motor sets and the electrical power pack to:

cause the first motor set to position the second and third motor sets relative to the sample plate at a first position, and in the first position cause the third motor set to move the magnetic bar sleeve frame from a position above the sample plate to a position wherein the plurality of magnetic bar sleeves are in contact with the fluid samples in the first row of wells, and to cause the magnetic bar sleeve frame and magnetic bar sleeves to vibrate for a preset time when the plurality of magnetic bar sleeves are in contact with the fluid samples, cause the second motor set to move the magnetic bar frame from a position above the sample plate to a position wherein the plurality of magnetic bars are inserted through the magnetic bar sleeves that are in contact with the fluid samples, thereby causing the magnetic ball within each sample well to attach to the corresponding magnetic bar sleeve, and cause the second and third motor sets to move each of the magnetic bar frame and the magnetic bar sleeve frame together to a position above the sample plate;

cause the first motor set to position the second and third motor sets relative to the sample plate at a second position, and in the second position,
  cause the second and third motor sets to move each of the magnetic bar frame and the magnetic bar sleeve frame together to a position wherein the plurality of magnetic bar sleeves and the plurality of magnetic bars are in contact with the washing reagent in the second row of wells, and
  cause the second and third motor sets to move each of the magnetic bar frame and the magnetic bar sleeve frame together to a position above the sample plate;
cause the first motor set to position the second and third motor sets relative to the sample plate at a third position, and in the third position,
  cause the second and third motor sets to move each of the magnetic bar frame and the magnetic bar sleeve frame together to a position wherein the plurality of magnetic bar sleeves and the plurality of magnetic bars are in contact with the elution reagent in the third row of wells, and
  cause the second and third motor sets to move each of the magnetic bar frame and the magnetic bar sleeve frame together to a position above the sample plate;
cause the first motor set to position the second and third motor sets relative to the sample plate at a fourth position, and in the fourth position,
  cause the second and third motor sets to move each of the magnetic bar frame and the magnetic bar sleeve frame together to a position wherein the plurality of magnetic bar sleeves and the plurality of magnetic bars are within the fourth row of wells, and
  cause the second motor set to move the magnetic bar frame from a position above the sample plate to a position wherein the plurality of magnetic bars are withdrawn from the magnetic bar sleeves.

2. The nucleic acid extraction instrument according to claim 1, wherein
  the first motor is fixed on the base and incapable of generating a relative displacement of the first motor relative to the base,
  the first motor is operably connected to a first motor shaft configured to rotate when driven by the first motor,
  a ball screw is coaxially connected with the first motor shaft via a connector and is configured to rotate along its axis when the first motor drives the first motor shaft,
  a sliding block is operably connected to the ball screw, and
  a guide rail is operably connected to the sliding block and configured to provide a track on which the sliding block moves when the first motor drives the first motor shaft.

3. The nucleic acid extraction instrument according to claim 2, wherein the second motor set and the third motor set are fixed to the sliding block of the first motor set and reciprocate along the ball screw axis when the first motor drives the first motor shaft.

4. The nucleic acid extraction instrument according to claim 2, wherein
  the second motor set and the third motor set are fixed to the sliding block of the first motor set via a motor bracket,
  the motor bracket comprises a first panel and a second panel approximately perpendicular to each other,
  the first panel is configured to fix the second motor set and the third motor set, and
  the second panel is fixed to the sliding block of the first motor set.

5. The nucleic acid extraction instrument according to claim 1, further comprising a bottom plate 32, an inner housing 34, a portal frame 36, and an operating platform 38, wherein the bottom plate, the inner housing, the portal frame, and the operating platform are fixed to the base.

* * * * *